US012579650B2

(12) United States Patent
Courot et al.

(10) Patent No.: US 12,579,650 B2
(45) Date of Patent: Mar. 17, 2026

(54) SPINAL HARDWARE RENDERING

(71) Applicant: GE Precision Healthcare LLC,
Waukesha, WI (US)

(72) Inventors: Adèle Marie Cécile Courot, Paris
(FR); Nicolas Gogin, Chatenay Malabry
(FR); Heber Hernandez, Salt Lake
City, UT (US); Quang Minh Nguyen,
Paris (FR)

(73) Assignee: **GE PRECISION HEALTHCARE
LLC**, Waukesha, WI (US)

( * ) Notice: Subject to any disclaimer, the term of this
patent is extended or adjusted under 35
U.S.C. 154(b) by 319 days.

(21) Appl. No.: 18/501,375

(22) Filed: Nov. 3, 2023

(65) Prior Publication Data

US 2024/0169538 A1 May 23, 2024

Related U.S. Application Data

(60) Provisional application No. 63/384,290, filed on Nov.
18, 2022.

(51) Int. Cl.
G06T 7/00 (2017.01)
G16H 30/20 (2018.01)
(52) U.S. Cl.
CPC ........... G06T 7/0014 (2013.01); G16H 30/20
(2018.01)
(58) Field of Classification Search
CPC .............................. G06T 7/0014; G16H 30/20
See application file for complete search history.

(56) References Cited

U.S. PATENT DOCUMENTS

| | | | |
|---|---|---|---|
| 7,194,120 B2 | 3/2007 | Wicker et al. | |
| 7,235,076 B2 | 6/2007 | Pacheco | |
| 8,891,847 B2 | 11/2014 | Helm et al. | |
| 9,216,048 B2 | 12/2015 | Markey et al. | |
| 9,545,233 B2 | 1/2017 | Sirpad et al. | |
| 10,390,886 B2 | 8/2019 | Li et al. | |
| 11,367,179 B2 * | 6/2022 | Polzin .................. | G06N 3/0464 |

(Continued)

FOREIGN PATENT DOCUMENTS

WO        2006039809 A1      4/2006

OTHER PUBLICATIONS

Rajaee, et al. "National trends in revision spinal fusion in the USA"
The Bone & Joint Journal, vol. 96-B, No. 6, Jun. 2014, 10 pages.

(Continued)

*Primary Examiner* — Mohammed H Zuberi
(74) *Attorney, Agent, or Firm* — Amin, Turocy & Watson,
LLP

(57) ABSTRACT

Systems/techniques that facilitate improved spinal hardware
rendering are provided. In various embodiments, a system
can access a medical imaging voxel array depicting a spine
of a medical patient. In various aspects, the system can
determine whether the medical imaging voxel array depicts
a set of surgical hardware inserted in the spine of the medical
patient. In various instances, the system can, in response to
a determination that the medical imaging voxel array depicts
the set of surgical hardware, localize a surface that sagittally
bisects the spine of the medical patient. In various cases, the
system can render, on an electronic display, a butterfly-view
of the medical imaging voxel array, wherein the butterfly-
view can be hinged about the localized surface.

17 Claims, 22 Drawing Sheets

(56) References Cited

U.S. PATENT DOCUMENTS

| | | | |
|---|---|---|---|
| 2008/0118115 A1 | 5/2008 | Williamson | |
| 2012/0008845 A1 | 1/2012 | Ning et al. | |
| 2013/0131819 A1* | 5/2013 | Parisi | A61F 2/38 |
| | | | 623/20.33 |
| 2014/0276001 A1 | 9/2014 | Ungi et al. | |
| 2016/0260231 A1* | 9/2016 | Klinder | G06T 11/008 |
| 2020/0022609 A1* | 1/2020 | Lorenz | A61B 6/032 |
| 2020/0405395 A1* | 12/2020 | Gullotti | A61B 17/809 |
| 2022/0101048 A1* | 3/2022 | Tan | A61B 5/055 |
| 2022/0292672 A1* | 9/2022 | Shirazian | G06T 7/11 |
| 2023/0111306 A1* | 4/2023 | Anand | G06T 7/0014 |
| | | | 382/128 |
| 2023/0139841 A1* | 5/2023 | DiMarco | G06T 19/00 |
| | | | 345/419 |
| 2023/0386153 A1* | 11/2023 | Rybnikov | G02B 27/01 |

OTHER PUBLICATIONS

Grotle, et al. "Lumbar spine surgery across 15 years: trends, complications and reoperations in a longitudinal observational study from Norway" BMJ Open 2019;9:e028743. doi:10.1136/bmjopen-2018-028743, 2019, 7 pages.
Brook, et al. "Trends in Lumbar Fusion Procedure Rates and Associated Hospital Costs for Degenerative Spinal Diseases in the United States, 2004 to 2015" Spine vol. 44, No. 5, pp. 369-376, 2018, 8 Pages.

* cited by examiner

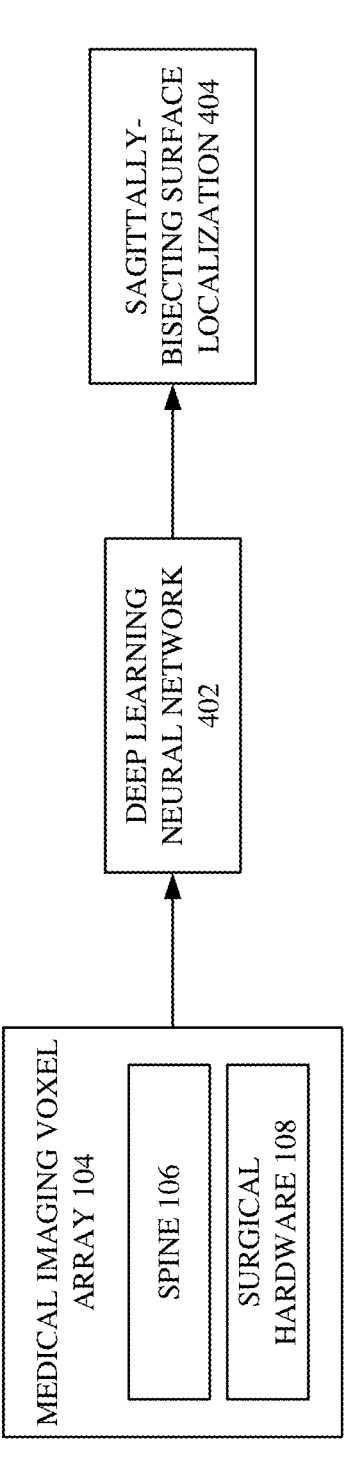
FIG. 5

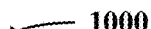
1002
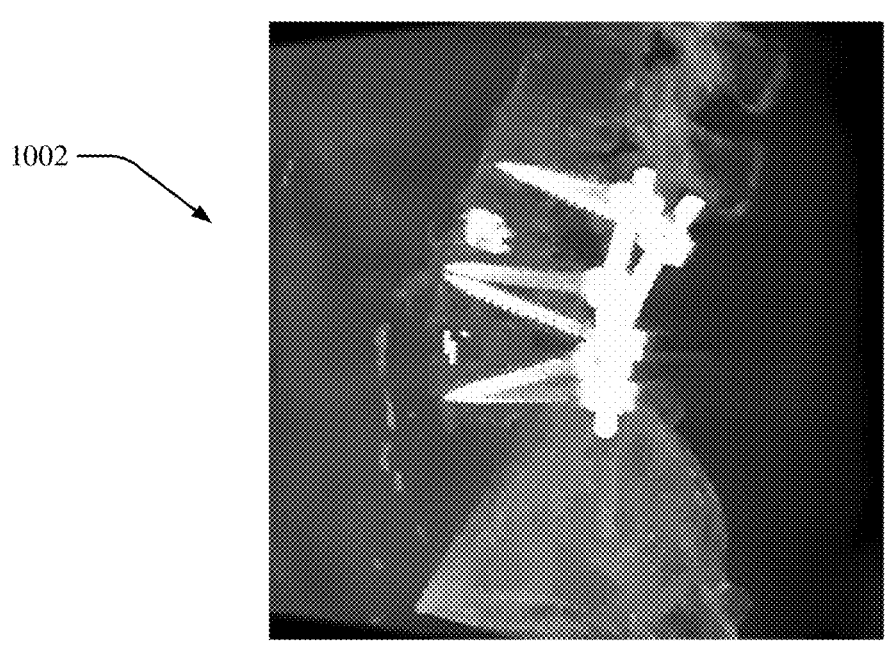
1004
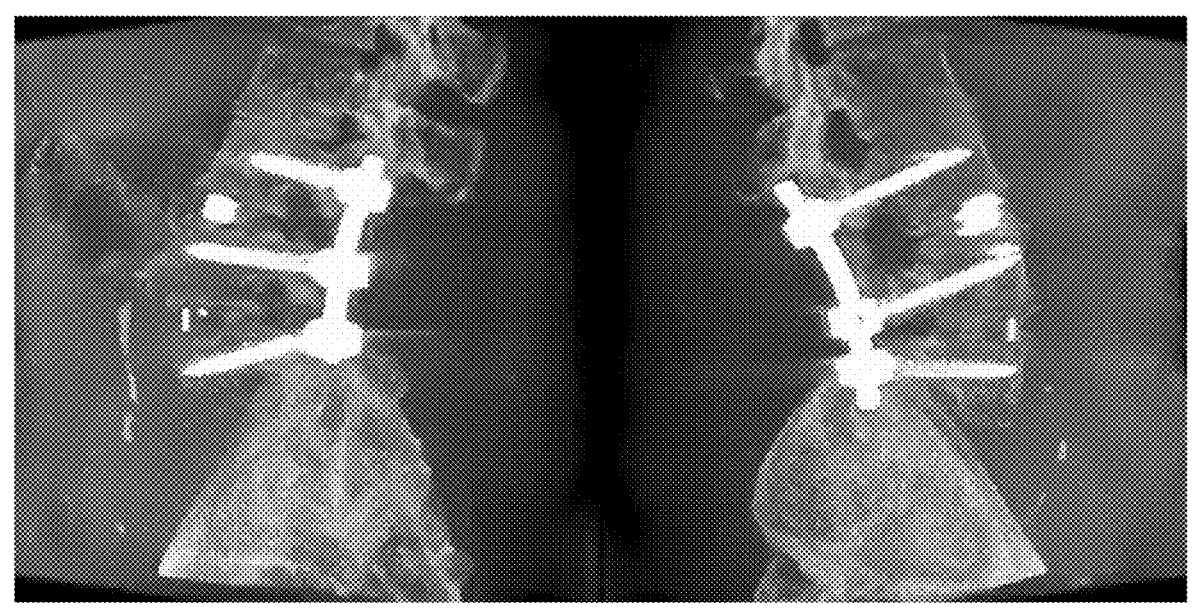
FIG. 10

1100
1102
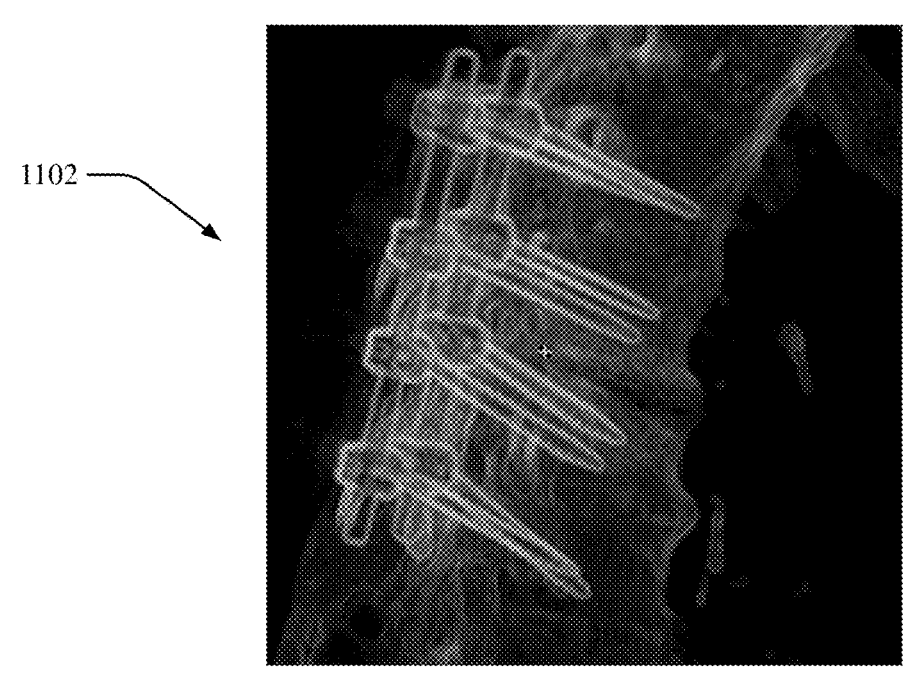
1104
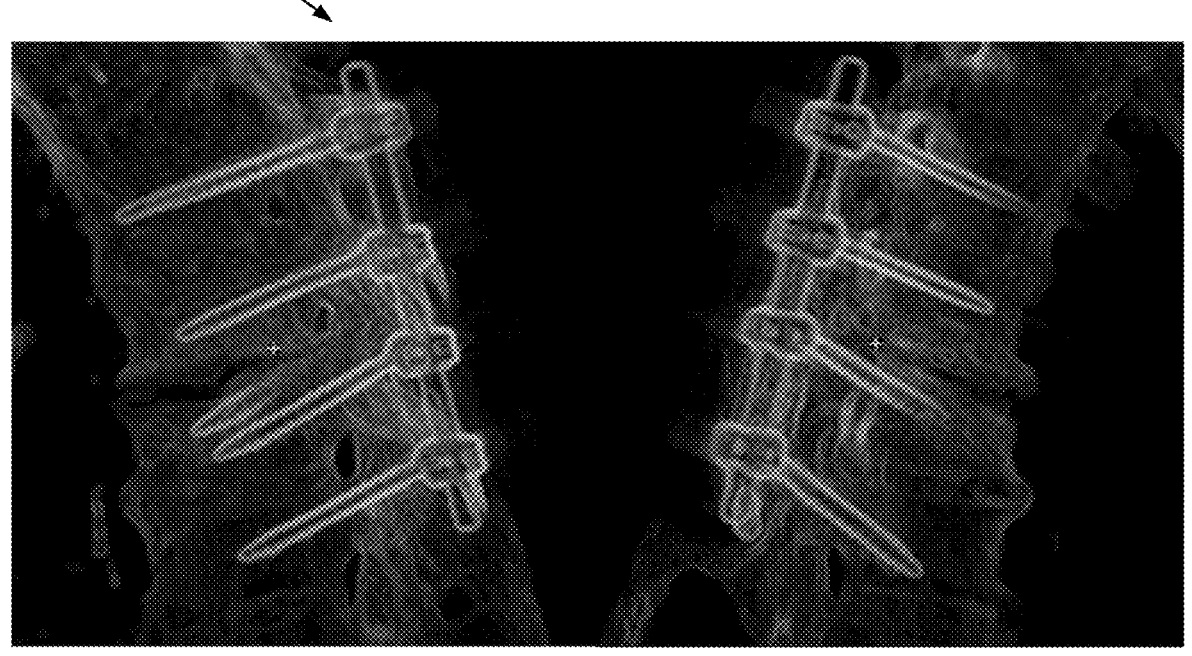
FIG. 11

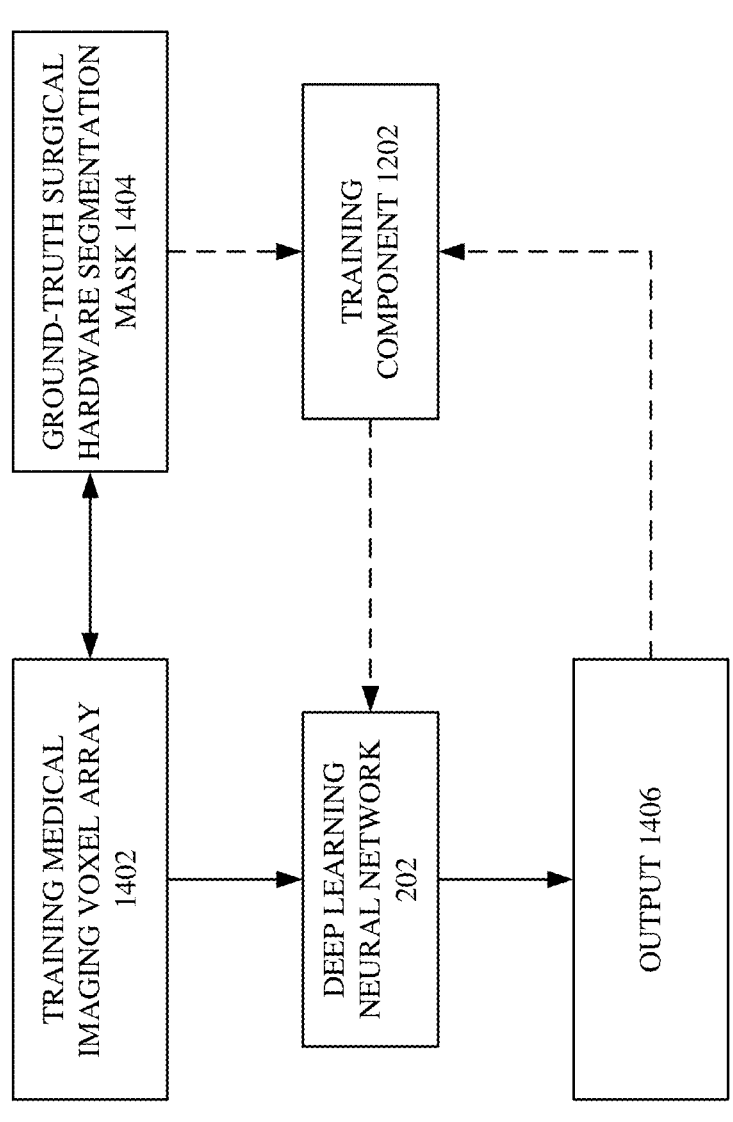
1400
GROUND-TRUTH SURGICAL HARDWARE SEGMENTATION MASK 1404
TRAINING COMPONENT 1202
TRAINING MEDICAL IMAGING VOXEL ARRAY 1402
DEEP LEARNING NEURAL NETWORK 202
OUTPUT 1406
FIG. 14

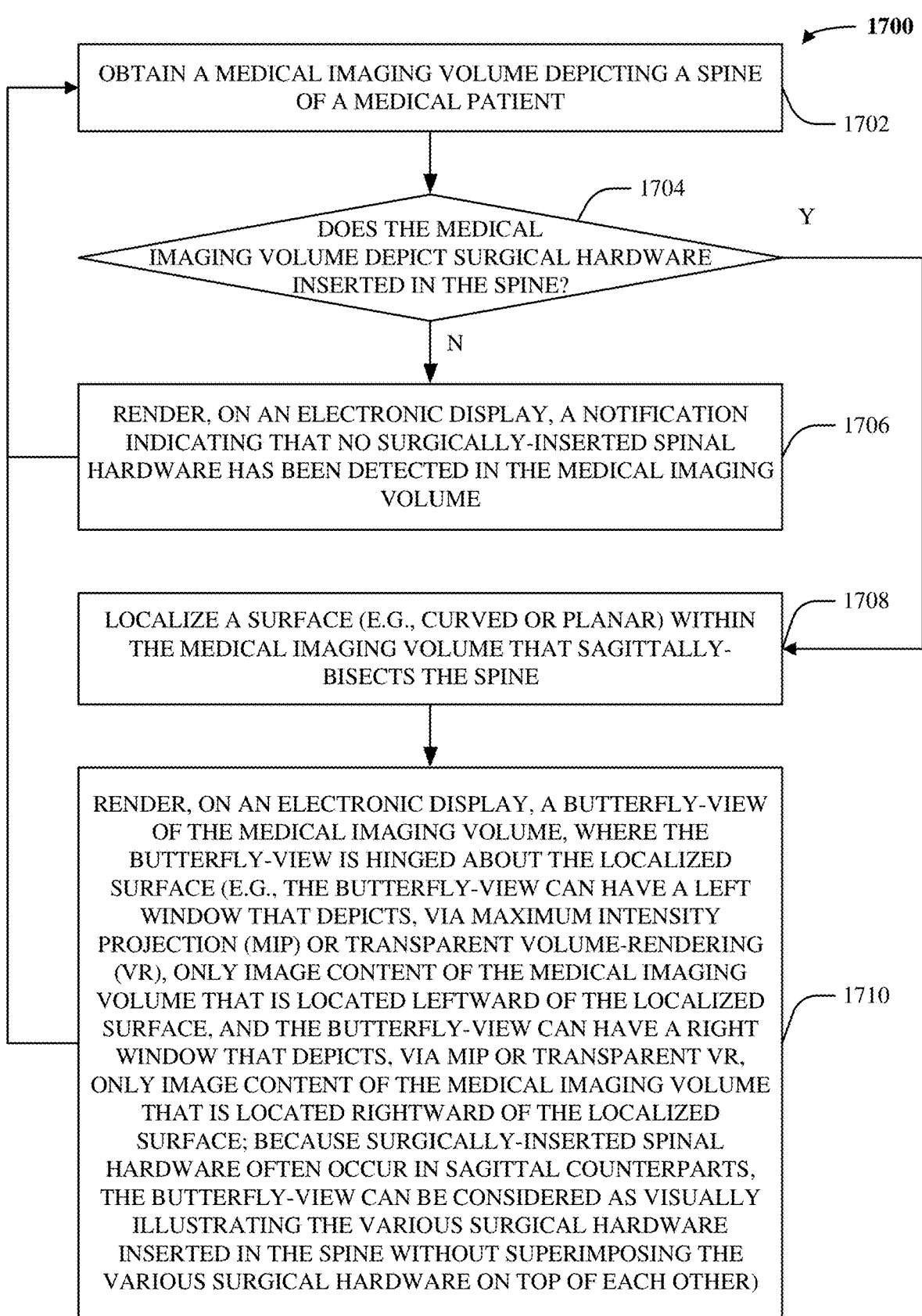

1700

OBTAIN A MEDICAL IMAGING VOLUME DEPICTING A SPINE OF A MEDICAL PATIENT

1702

DOES THE MEDICAL IMAGING VOLUME DEPICT SURGICAL HARDWARE INSERTED IN THE SPINE?

1704

Y

N

RENDER, ON AN ELECTRONIC DISPLAY, A NOTIFICATION INDICATING THAT NO SURGICALLY-INSERTED SPINAL HARDWARE HAS BEEN DETECTED IN THE MEDICAL IMAGING VOLUME

1706

LOCALIZE A SURFACE (E.G., CURVED OR PLANAR) WITHIN THE MEDICAL IMAGING VOLUME THAT SAGITTALLY-BISECTS THE SPINE

1708

RENDER, ON AN ELECTRONIC DISPLAY, A BUTTERFLY-VIEW OF THE MEDICAL IMAGING VOLUME, WHERE THE BUTTERFLY-VIEW IS HINGED ABOUT THE LOCALIZED SURFACE (E.G., THE BUTTERFLY-VIEW CAN HAVE A LEFT WINDOW THAT DEPICTS, VIA MAXIMUM INTENSITY PROJECTION (MIP) OR TRANSPARENT VOLUME-RENDERING (VR), ONLY IMAGE CONTENT OF THE MEDICAL IMAGING VOLUME THAT IS LOCATED LEFTWARD OF THE LOCALIZED SURFACE, AND THE BUTTERFLY-VIEW CAN HAVE A RIGHT WINDOW THAT DEPICTS, VIA MIP OR TRANSPARENT VR, ONLY IMAGE CONTENT OF THE MEDICAL IMAGING VOLUME THAT IS LOCATED RIGHTWARD OF THE LOCALIZED SURFACE; BECAUSE SURGICALLY-INSERTED SPINAL HARDWARE OFTEN OCCUR IN SAGITTAL COUNTERPARTS, THE BUTTERFLY-VIEW CAN BE CONSIDERED AS VISUALLY ILLUSTRATING THE VARIOUS SURGICAL HARDWARE INSERTED IN THE SPINE WITHOUT SUPERIMPOSING THE VARIOUS SURGICAL HARDWARE ON TOP OF EACH OTHER)

1900
1004
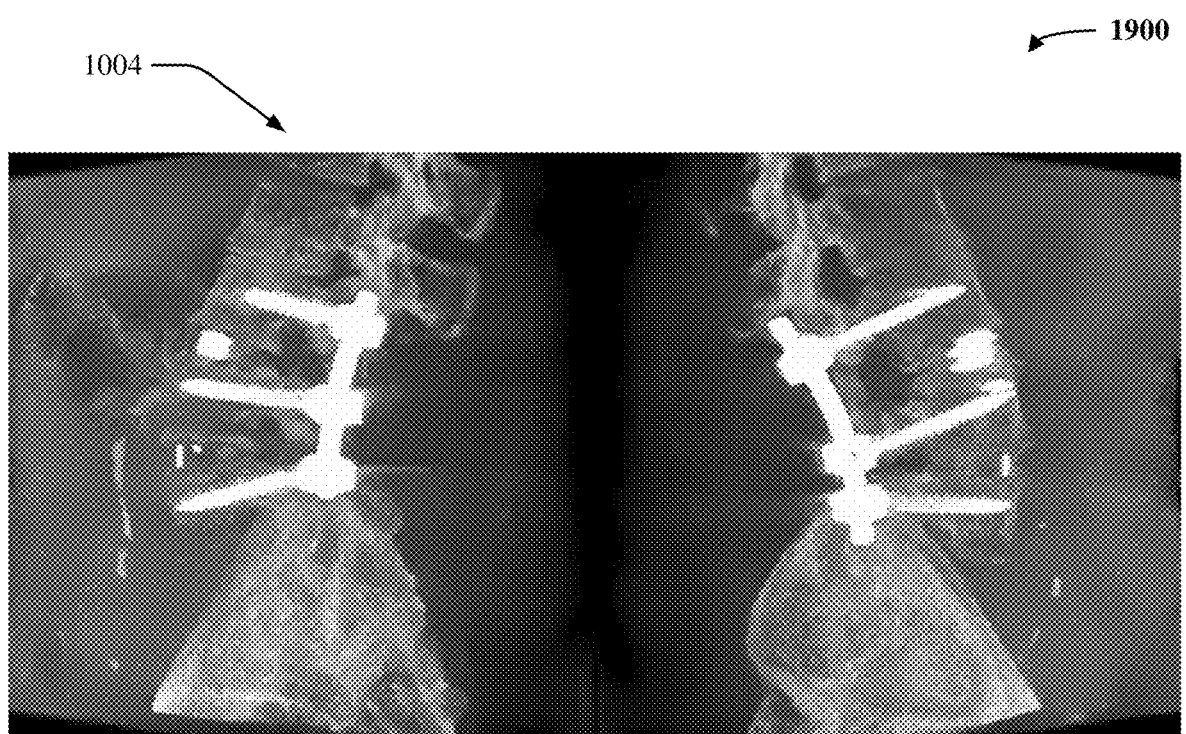
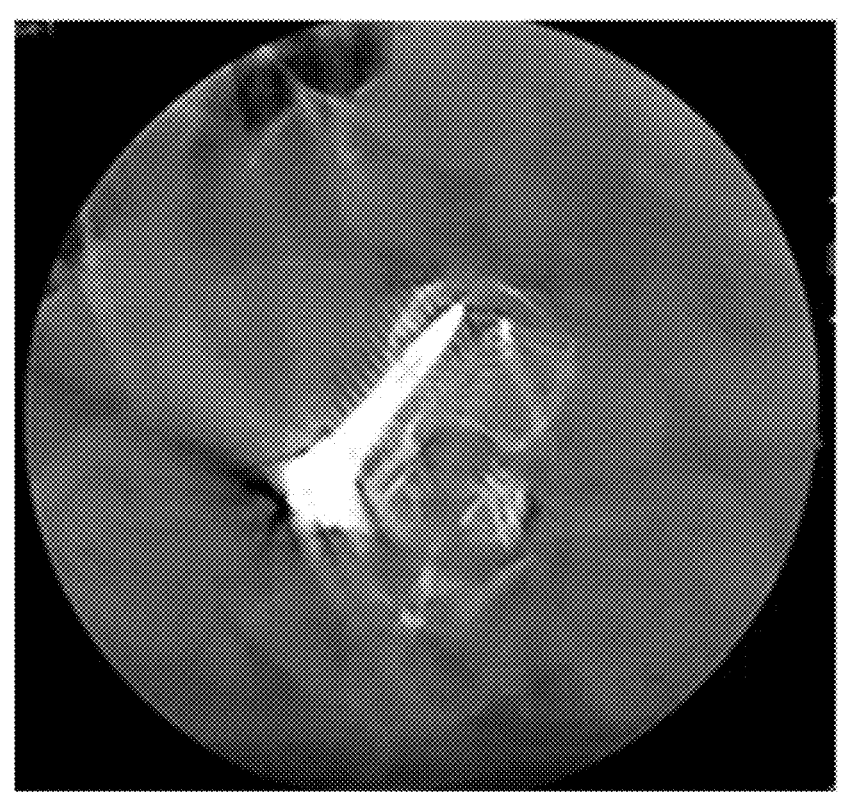
1902
FIG. 19

2000

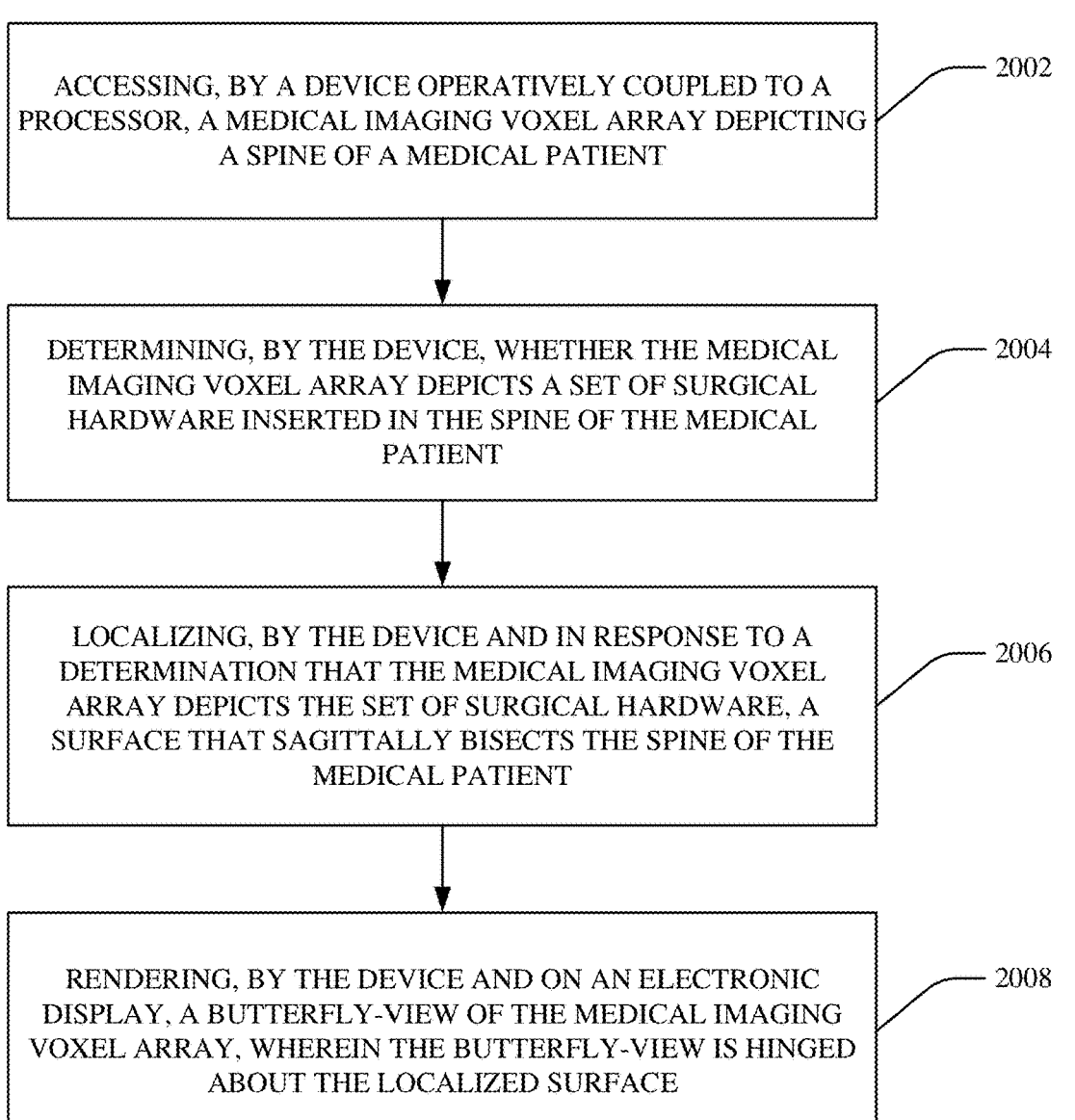

ACCESSING, BY A DEVICE OPERATIVELY COUPLED TO A PROCESSOR, A MEDICAL IMAGING VOXEL ARRAY DEPICTING A SPINE OF A MEDICAL PATIENT — 2002

DETERMINING, BY THE DEVICE, WHETHER THE MEDICAL IMAGING VOXEL ARRAY DEPICTS A SET OF SURGICAL HARDWARE INSERTED IN THE SPINE OF THE MEDICAL PATIENT — 2004

LOCALIZING, BY THE DEVICE AND IN RESPONSE TO A DETERMINATION THAT THE MEDICAL IMAGING VOXEL ARRAY DEPICTS THE SET OF SURGICAL HARDWARE, A SURFACE THAT SAGITTALLY BISECTS THE SPINE OF THE MEDICAL PATIENT — 2006

RENDERING, BY THE DEVICE AND ON AN ELECTRONIC DISPLAY, A BUTTERFLY-VIEW OF THE MEDICAL IMAGING VOXEL ARRAY, WHEREIN THE BUTTERFLY-VIEW IS HINGED ABOUT THE LOCALIZED SURFACE — 2008

FIG. 20

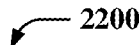
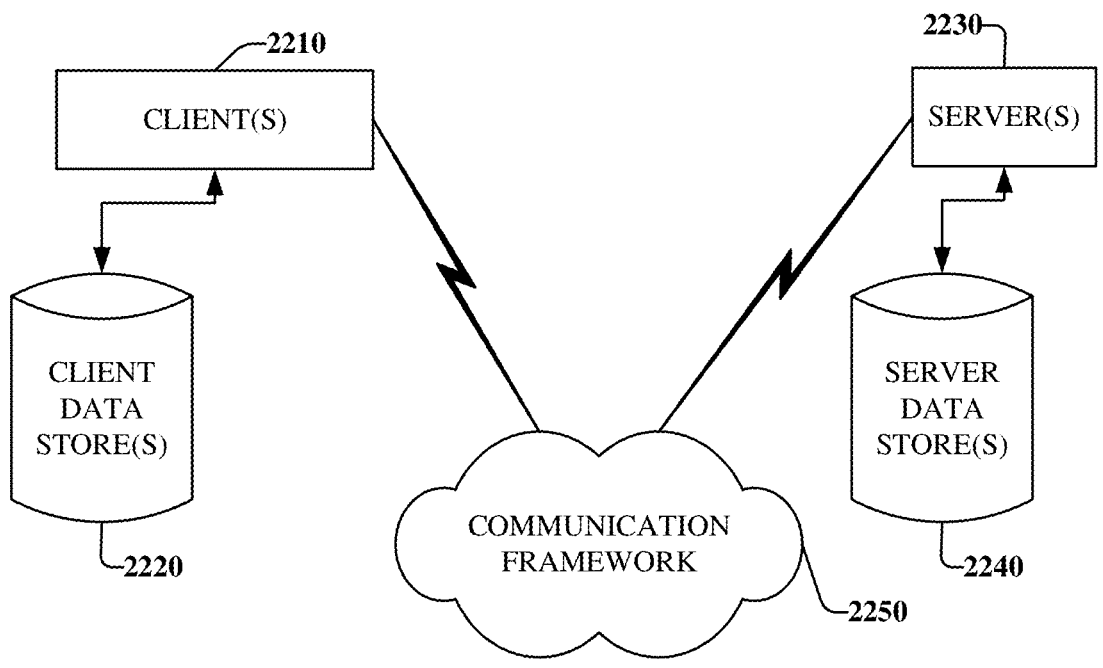
FIG. 22

SPINAL HARDWARE RENDERING

RELATED APPLICATION

This application claims priority to U.S. Provisional Patent Application No. 63/384,290, filed Nov. 18, 2022, and entitled "IMPROVED SPINAL HARDWARE RENDERING", the entirety of which is incorporated herein by reference.

TECHNICAL FIELD

The subject disclosure relates generally to medical imaging, and more specifically to improved spinal hardware rendering.

BACKGROUND

Various surgical procedures can involve inserting hardware into the spine of a medical patient. Medical visualization techniques can be implemented to check whether such hardware is properly positioned or oriented. Unfortunately, existing techniques for visualizing such hardware rely significantly on manual intervention and suffer from superimposition-based visual clutter.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate improved spinal hardware rendering are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a medical imaging voxel array depicting a spine of a medical patient. In various aspects, the computer-executable components can comprise a hardware component that can determine whether the medical imaging voxel array depicts a set of surgical hardware inserted in the spine of the medical patient. In various instances, the computer-executable components can comprise a surface component that can, in response to a determination that the medical imaging voxel array depicts the set of surgical hardware, localize a surface that sagittally bisects the spine of the medical patient. In various cases, the computer-executable components can comprise a visualization component that can render, on an electronic display, a butterfly-view of the medical imaging voxel array, wherein the butterfly-view is hinged about the localized surface.

According to one or more embodiments, the above-described system can be implemented as a computer-implemented method or a computer program product.

DESCRIPTION OF THE DRAWINGS

FIG. 5 illustrates an example, non-limiting block diagram showing how a deep learning neural network can generate a sagittally-bisecting surface localization in accordance with one or more embodiments described herein.

FIGS. 10-11 illustrate non-limiting examples of butterfly-views in accordance with one or more embodiments described herein.

FIG. 14 illustrates an example, non-limiting block diagram showing how a deep learning neural network can be trained to generate surgical hardware segmentation masks in accordance with one or more embodiments described herein.

FIG. 17 illustrates a flow diagram of an example, non-limiting computer-implemented method that facilitates improved spinal hardware rendering in accordance with one or more embodiments described herein.

FIG. 19 illustrates a non-limiting example of an auxiliary viewport in accordance with one or more embodiments described herein.

FIG. 20 illustrates a flow diagram of an example, non-limiting computer-implemented method that facilitates improved spinal hardware rendering in accordance with one or more embodiments described herein.

FIG. 22 illustrates an example networking environment operable to execute various implementations described herein.

DETAILED DESCRIPTION

Figure 1:
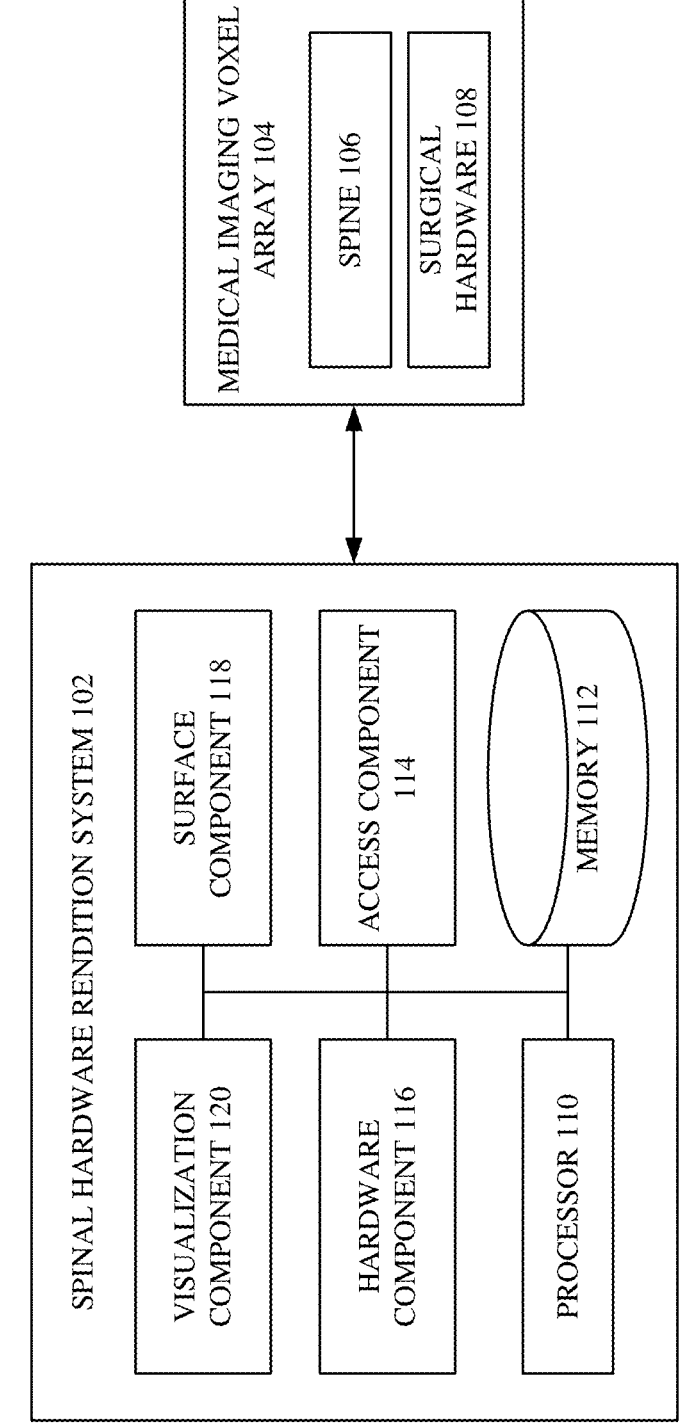
FIG. 1 illustrates a block diagram of an example, non-limiting system that facilitates improved spinal hardware rendering in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Various surgical procedures can involve inserting hardware into the spine of a medical patient. For example, spinal fusion can be an orthopedic surgical technique that joins two or more spinal vertebrae together via a bone graft, where screws, rods, plates, or other metallic hardware can be implemented to physically hold the two or more spinal vertebrae together while the bone graft cures or matures. In any case, proper positioning or orientation of such hardware can be required in order for such surgical procedures to be successful.

Various medical imaging technologies (e.g., computed tomography (CT) scanning, magnetic resonance imaging (MRI) scanning. X-ray scanning, ultrasound scanning, positron emission tomography (PET) scanning) can be implemented to visualize such hardware within the spine of the medical patient, and such visualizations can be leveraged to verify the positions or orientations of such hardware. In other words, scanned medical images depicting such hardware within the spine of the medical patient can be captured, and medical professionals can visually inspect such scanned medical images to check whether such hardware is properly positioned or oriented within the spine of the medical patient.

Unfortunately, existing techniques for rendering or otherwise visualizing surgically-inserted spinal hardware suffer from various disadvantages.

First, such existing techniques rely substantially on manual intervention by an attendant medical professional. In particular, when given a medical imaging volume (e.g., an array of voxels) depicting a plurality of hardware inserted into the spine of a medical patient, the attendant medical professional often cannot sufficiently inspect a desired one of the plurality of hardware without manually scrolling, translating, or rotating the medical imaging volume so that the desired one of the plurality of hardware is being viewed from a particular perspective or projection. Performing such manual scrolling, translating, or rotating for a single piece of surgically-inserted spinal hardware can be time-consuming and cumbersome. Accordingly, performing such manual scrolling, translating, or rotating for a plurality of surgically-inserted spinal hardware (e.g., tens or dozens of pieces of hardware can be inserted into the spine of a single medical patient) can be even more so.

Second, such existing techniques often generate visualizations that superimpose multiple pieces of surgically-inserted spinal hardware on top of each other. More specifically, surgically-inserted spinal hardware are often inserted in a front-to-back direction of a medical patient (e.g., longitudinal axes of spinal screws can often extend back-to-front rather than up-to-down or left-to-right). Accordingly, when given a medical imaging volume depicting a plurality of hardware inserted into the spine of the medical patient, the positions or orientations of such plurality of hardware can be inspected by a medical professional via a sagittal projection of the medical imaging volume. However, surgically-inserted spinal hardware often can also be inserted as sagittal counterparts or sagittal pairs (e.g., one spinal screw inserted on the left side of a vertebra, and a corresponding spinal screw inserted on the right side of the vertebra; one spinal rod inserted on the left side of the spine, and a corresponding spinal rod inserted on the right side of the spine). Thus, a sagittal projection of the medical imaging volume can depict such sagittal counterparts or sagittal pairs as being superimposed on top of each other. Such superimposition can yield a cluttered, confusing view of the plurality of hardware, which can impede the medical professional's ability to visually inspect the positions or orientations of such hardware.

Accordingly, systems or techniques that can address one or more of these technical problems can be desirable.

Various embodiments described herein can address one or more of these technical problems. One or more embodiments described herein can include systems, computer-implemented methods, apparatus, or computer program products that can facilitate improved spinal hardware rendering. In other words, the inventors of various embodiments described herein devised various techniques for rendering or otherwise visualizing surgically-inserted spinal hardware, which techniques do not rely upon manual intervention or suffer from superimposition clutter. In particular, when given a medical imaging voxel array that depicts a spine of a medical patient, various embodiments described herein can involve automatically generating (e.g., via deep learning) a butterfly-view of the medical imaging voxel array. As described herein, the butterfly-view can be considered as an improved visualization layout that can illustrate surgical hardware that has been inserted into the spine of the medical patient, without superimposing such surgical hardware on top of each other, and thus without the clutter or confusion caused by superimposition. Accordingly, a medical professional can easily visually inspect such butterfly-view to determine whether or not the surgical hardware are properly positioned or oriented.

Various embodiments described herein can be considered as a computerized tool (e.g., any suitable combination of computer-executable hardware or computer-executable software) that can facilitate improved spinal hardware rendering. In various aspects, such computerized tool can comprise an access component, a hardware component, a surface component, or a visualization component.

In various embodiments, there can be a medical imaging volume. In various aspects, the medical imaging volume can be considered as a three-dimensional voxel array having any suitable number or arrangement of voxels. In various instances, the medical imaging volume can have been generated by any suitable medical imaging device (e.g., by a CT scanner, by an MRI scanner, by an X-ray scanner, by an ultrasound scanner, by a PET scanner). In various cases, the medical imaging volume can have been generated according to any suitable image reconstruction techniques (e.g., filtered backprojection).

In any case, the medical imaging volume can depict a spine (or any suitable portion thereof) of a medical patient (e.g., human, animal, or otherwise). Furthermore, in various aspects, the medical imaging volume can depict any suitable number of pieces of surgical hardware (e.g., screws, rods, plates) that have been inserted into the spine of the medical patient (e.g., inserted into various vertebrae of the medical patient).

In various aspects, it can be desired for a medical professional to visually inspect the intra-spinal positions or orientations of the surgical hardware. As described herein, the computerized tool can automatically render a specialized view (e.g., a specialized visualization layout) of the medical imaging volume, which specialized view can help to ease or quicken such visual inspection. As described herein, such specialized view can be referred to as a butterfly-view.

In various embodiments, the access component of the computerized tool can electronically receive or otherwise electronically access the medical imaging volume. In some aspects, the access component can electronically retrieve the medical imaging volume from any suitable centralized or decentralized data structures (e.g., graph data structures, relational data structures, hybrid data structures), whether remote from or local to the access component. In other aspects, the access component can electronically retrieve the medical imaging volume from whatever medical imaging device (e.g., CT scanner, MRI scanner, X-ray scanner, ultrasound scanner, PET scanner) generated or captured the medical imaging volume. In any case, the access component can electronically obtain or access the medical imaging volume, such that other components of the computerized tool can electronically interact with (e.g., read, write, edit, copy, manipulate) the medical imaging volume.

In various embodiments, the hardware component of the computerized tool can electronically confirm whether or not the medical imaging volume actually depicts the surgical hardware. In some cases, the hardware component can perform such confirmation via deep learning.

For example, in various instances, the hardware component can electronically store, maintain, control, or otherwise access a first deep learning neural network. In various aspects, the first deep learning neural network can exhibit any suitable internal architecture. For example, the first deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the first deep learning neural network can include any suitable numbers of neurons in various layers (e.g., different layers can have the same or different numbers of neurons as each other). As yet another example, the first deep learning neural network can include any suitable activation functions (e.g., softmax, sigmoid, hyperbolic tangent, rectified linear unit) in various neurons (e.g., different neurons can have the same or different activation functions as each other). As still another example, the first deep learning neural network can include any suitable interneuron connections or interlayer connections (e.g., forward connections, skip connections, recurrent connections).

In any case, the first deep learning neural network can be configured, as described herein, to receive as input medical imaging voxel arrays and to produce as output surgical hardware segmentation masks corresponding to such inputted medical imaging voxel arrays. Accordingly, the hardware component can electronically execute the first deep learning neural network on the medical imaging volume, thereby yielding a surgical hardware segmentation mask corresponding to the medical imaging volume. More specifically, the hardware component can feed the medical imaging volume to an input layer of the first deep learning neural network, the medical imaging volume can complete a forward pass through one or more hidden layers of the first deep learning neural network, and an output layer of the first deep learning neural network can compute the surgical hardware segmentation mask based on activations generated by the one or more hidden layers of the first deep learning neural network.

In various aspects, the surgical hardware segmentation mask can be any suitable electronic data that indicates which voxels of the medical imaging volume belong to or otherwise make up the surgical hardware that is inserted in the spine of the medical patient and which voxels of the medical imaging volume do not belong to or otherwise make up the surgical hardware. In various instances, the surgical hardware segmentation mask can exhibit the same format, size, or dimensionality as the medical imaging volume. For example, if the medical imaging volume is an a-by-b-by-c array of voxels for any suitable positive integers a, b, and c, then the surgical hardware segmentation mask can be an a-by-b-by-c array, where each element of such array can indicate whether or not a respective voxel of the medical imaging volume belongs to or otherwise makes up the surgical hardware. In other words, the surgical hardware segmentation mask can be considered as indicating voxel-wise classification labels for the medical imaging volume, where such a voxel-wise classification label can indicate a hardware class or a background class (in some cases, however, more than two voxel classes can be implemented).

In various embodiments, the hardware component can determine whether or not the medical imaging voxel array actually depicts the surgical hardware, by analyzing the surgical hardware segmentation mask. For example, if the surgical hardware segmentation mask indicates that no voxels (or that fewer than any suitable threshold number of voxels) of the medical imaging volume belong to the surgical hardware class, then the hardware component can conclude that the medical imaging volume does not actually depict any surgical hardware inserted into the spine of the medical patient. On the other hand, if the surgical hardware segmentation mask indicates that at least one voxel (or more than any suitable threshold number of voxels) of the medical imaging volume belong to the surgical hardware class, then the hardware component can conclude that the medical imaging volume does actually depict some surgical hardware inserted into the spine of the medical patient.

In various embodiments, if the hardware component determines that the medical imaging volume does not actually depict surgical hardware inserted in the spine of the medical patient, then the visualization component of the computerized tool can electronically render any suitable notification or message to that effect on any suitable computer screen, display, or monitor.

In various embodiments, if the hardware component instead determines that the medical imaging volume does actually depict surgical hardware inserted in the spine of the medical patient, then the surface component of the computerized tool can electronically localize a surface within the medical imaging volume, which surface can sagittally-bisect the spine of the medical patient. In some cases, the surface component can perform such localization via deep learning.

For example, in various instances, the surface component can electronically store, maintain, control, or otherwise access a second deep learning neural network. In various aspects, the second deep learning neural network can exhibit any suitable internal architecture. For example, the second deep learning neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the second deep learning neural network can include any suitable numbers of neurons in various layers (e.g., different layers can have the same or different numbers of neurons as each other). As yet another example, the second deep learning neural network can include any suitable activation functions (e.g., softmax, sigmoid, hyperbolic tangent, rectified linear unit) in various neurons (e.g., different neurons can have the same or different activation functions as each other). As still another example, the second deep learning neural network can include any suitable interneuron connections or interlayer connections (e.g., forward connections, skip connections, recurrent connections).

In any case, the second deep learning neural network can be configured, as described herein, to receive as input medical imaging voxel arrays and to localize as output sagittally-bisecting surfaces in such inputted medical imaging voxel arrays. Accordingly, the surface component can electronically execute the second deep learning neural network on the medical imaging volume, thereby yielding a sagittally-bisecting surface localization corresponding to the medical imaging volume. More specifically, the surface component can feed the medical imaging volume to an input layer of the second deep learning neural network, the medical imaging volume can complete a forward pass through one or more hidden layers of the second deep learning neural network, and an output layer of the second deep learning neural network can compute the sagittally-bisecting surface localization based on activations generated by the one or more hidden layers of the second deep learning neural network.

In various aspects, the sagittally-bisecting surface localization can be any suitable electronic data that indicates or otherwise identifies a planar or curved surface within the medical imaging volume, which planar or curved surface bisects (or substantially bisects) the spine of the medical patient into sagittal portions. In other words, such planar or curved surface can be considered as separating the spine of the medical patient into a left half and a right half. Note that, in some instances, the planar or curved surface can imperfectly bisect the spine of the medical patient into unequal or non-symmetric sagittal portions. That is, in various cases, the planar or curved surface can separate the spine into a left side and a right side, where the left side and the right side are not necessarily equal or symmetric to each other. Even in such case of imperfect bisection, the planar or curved surface can nevertheless be referred to as sagittally-bisecting the spine of the medical patient.

In various aspects, the sagittally-bisecting surface localization can exhibit any suitable format, size, or dimensionality. For example, in some cases, the sagittally-bisecting surface localization can be one or more parameters that collectively define the planar or curved surface that sagittally-bisects the spine (e.g., one or more x-axis parameters that indicate how the planar or curved surface varies along an x-axis of the medical imaging volume, one or more y-axis parameters that indicate how the planar or curved surface varies along a y-axis of the medical imaging volume, one or more z-axis parameters that indicate how the planar or curved surface varies along a z-axis of the medical imaging volume). As another example, the sagittally-bisecting surface localization can be a segmentation mask that indicates which voxels of the medical imaging volume belong to or otherwise make up the planar or curved surface and which voxels of the medical imaging volume do not belong to or otherwise make up the planar or curved surface. In such case, the sagittally-bisecting surface localization can exhibit the same format, size, or dimensionality as the medical imaging volume. That is, if the medical imaging volume is an a-by-b-by-c array of voxels, then the sagittally-bisecting surface localization can be an a-by-b-by-c array, where each element of such array can indicate whether or not a respective voxel of the medical imaging volume belongs to or otherwise makes up the planar or curved surface. In other words, the sagittally-bisecting surface localization can, in such case, be considered as indicating voxel-wise classification labels for the medical imaging volume, where such a voxel-wise classification label can indicate a sagittally-bisecting surface class or a background class (in some cases, however, more than two voxel classes can be implemented).

In various embodiments, the visualization component of the computerized tool can electronically render, on any suitable computer display, screen, or monitor, a butterfly-view of the medical imaging volume, based on the sagittally-bisecting surface localization. More specifically, the butterfly-view can have a left window and a right window. In various aspects, the left window can depict or otherwise illustrate voxels within the medical imaging volume that are located leftward of the planar or curved surface specified by the sagittally-bisecting surface localization, and the left window can exclude, not depict, or otherwise not illustrate voxels within the medical imaging volume that are located rightward of the planar or curved surface specified by the sagittally-bisecting surface localization. In other words, the left window can illustrate any suitable projection (e.g., generated via a maximum intensity projection (MIP) technique or a transparent volume-rendering (VR) projection technique) of the medical imaging volume, where such projection includes only voxels that are leftward of the planar or curved surface specified by the sagittally-bisecting surface localization. In contrast, the right window can depict or otherwise illustrate voxels within the medical imaging volume that are located rightward of the planar or curved surface specified by the sagittally-bisecting surface localization, and the right window can exclude, not depict, or otherwise not illustrate voxels within the medical imaging volume that are located leftward of the planar or curved surface specified by the sagittally-bisecting surface localization. That is, the right window can illustrate any suitable projection (e.g., generated via an MIP technique or a transparent VR projection technique) of the medical imaging volume, where such projection includes only voxels that are rightward of the planar or curved surface specified by the sagittally-bisecting surface localization. In some cases, the projection depicted in the left window and the projection depicted in the right window can be independently rotatable or translatable via user-input (e.g., user-input received by a mouse, keyboard, touchscreen, or voice command).

In various aspects, the left window can depict a sagittal projection of the voxels that are leftward of the planar or curved surface, and the right window can depict a sagittal projection of the voxels that are rightward of the planar or curved surface. In such case, the butterfly-view can be considered as the result obtained by slicing, along the planar or curved surface indicated by the sagittally-bisecting surface localization, the medical imaging volume into a left sub-volume and a right sub-volume, and geometrically folding, hinging, or otherwise swiveling both the left sub-volume and the right sub-volume outward about the planar or curved surface, likes the wings of a butterfly (hence the term "butterfly-view") or like the covers of a book.

In any case, the butterfly-view can visually illustrate or depict the surgical hardware inserted in the spine of the medical patient, without superimposing such surgical hardware on top of each other. More specifically, as mentioned above, surgical hardware can be inserted into the spine of the medical patient in sagittal pairs or sagittal counterparts, and so existing techniques for viewing a sagittal projection of such medical imaging volume would superimpose such sagittal pairs or sagittal counterparts over each other, which would yield a cluttered, confusing view. For instance, a first screw can be inserted into the left side of a vertebra depicted in the medical imaging volume, and a second screw can be inserted into the right side of that same vertebra. Accordingly, if a sagittal projection of such vertebra were implemented via existing techniques, the sagittal projection would superimpose the voxels making up the first screw on top of the voxels making up the second screw, and it would thus be difficult to verify the independent positions or orientations of the two screws.

In stark contrast, the butterfly-view can avoid such superimposition of sagittally-paired hardware. This is because sagittally-paired spinal hardware can often be located on opposite sagittal sides of the spine of the medical patient (e.g., one piece of hardware located on a left side of the spine of the medical patient, and a corresponding piece of hardware located on a right side of the spine of the medical patient). Accordingly, because the left window of the butterfly-view can illustrate only those voxels that are leftward of the planar or curved surface that sagittally-bisects the spine of the medical patient, no voxels that are rightward of the planar or curved surface can be superimposed on anything shown in the left window. Accordingly, none of the surgical hardware that is inserted in the right side of the spine of the medical patient can be superimposed on any surgical hardware that is depicted in the left window. In other words, any given piece of surgical hardware shown in the left window can be depicted without superimposition of another piece of surgical hardware that is sagittally-paired to that given piece of surgical hardware. Likewise, because the right window of the butterfly-view can illustrate only those voxels that are rightward of the planar or curved surface that sagittally-bisects the spine of the medical patient, no voxels that are leftward of the planar or curved surface can be superimposed on anything shown in the right window. Accordingly, none of the surgical hardware that is inserted in the left side of the spine of the medical patient can be superimposed on any surgical hardware that is depicted in the right window. In other words, any given piece of surgical hardware shown in the right window can be depicted without superimposition of another piece of surgical hardware that is sagittally-paired to that given piece of surgical hardware.

To help cause the surgical hardware segmentation mask to be accurate, the first deep learning neural network can undergo any suitable type or paradigm of training (e.g., supervised training, unsupervised training, reinforcement learning). Accordingly, in various aspects, the access component can receive, retrieve, or otherwise access a first training dataset, and the computerized tool can comprise a training component that can train the first deep learning neural network on the first training dataset.

In some instances, the first training dataset can be annotated. In such cases, the first training dataset can include a first set of training medical imaging volumes and a set of ground-truth segmentation masks that respectively correspond to the first set of training medical imaging volumes. In various aspects, a training medical imaging volume can be any suitable electronic data having the same format, size, or dimensionality as the medical imaging volume described above. Accordingly, a training medical imaging volume can be considered as a voxel array having the same number or arrangement of voxels as the medical imaging volume discussed above. Moreover, in various instances, each training medical imaging volume can depict a respective spine of a respective medical patient, and such respective spine may or may not have various surgical hardware inserted therewith.

In various aspects, a ground-truth segmentation mask can be any suitable electronic data having the same format, size, or dimensionality as the surgical hardware segmentation mask discussed above. Accordingly, a ground-truth segmentation mask can indicate which voxels (if any) of a respective training medical imaging volume are known or otherwise deemed to belong to surgically-inserted spinal hardware depicted in the respective training medical imaging volume.

If the first training dataset is annotated, then the training component can, in various aspects, perform supervised training on the first deep learning neural network. Prior to the start of such supervised training, the training component can randomly initialize internal parameters (e.g., weights, biases, convolutional kernels) of the first deep learning neural network.

In various aspects, the training component can select from the first training dataset any suitable training medical imaging volume and any suitable ground-truth segmentation mask corresponding to such selected training medical imaging volume. In various instances, the training component can execute the first deep learning neural network on the selected training medical imaging volume, thereby causing the first deep learning neural network to produce some output. For example, the training component can feed the selected training medical imaging volume to an input layer of the first deep learning neural network, the selected training medical imaging volume can complete a forward pass through one or more hidden layers of the first deep learning neural network, and an output layer of the first deep learning neural network can compute the output based on activations generated by the one or more hidden layers. Note that, in various cases, the dimensionality of the output can be controlled or otherwise determined by the number of neurons in the output layer (e.g., an output of a desired size can be achieved by adding neurons to or removing neurons from the output layer). In any case, the output can be considered as the predicted or inferred surgical hardware segmentation mask that the first deep learning neural network identifies as corresponding to the selected training medical imaging volume. In contrast, the selected ground-truth segmentation mask can be considered as the correct or accurate surgical hardware segmentation mask that is known or deemed to correspond to the selected training medical imaging volume. Note that, if the first deep learning neural network has so far undergone no or little training, then the output can be highly inaccurate (e.g., can be highly different from the selected ground-truth segmentation mask). In various aspects, the training component can compute one or more errors or losses (e.g., mean absolute error (MAE), mean squared error (MSE), cross-entropy) between the output and the selected ground-truth segmentation mask. In various instances, the training component can update the internal parameters of the first deep learning neural network by performing backpropagation (e.g., stochastic gradient descent) driven by the one or more errors or losses.

In various instances, such supervised training procedure can be repeated for each training medical imaging volume in the first training dataset, with the result being that the internal parameters of the first deep learning neural network can become iteratively optimized to accurately generate surgical hardware segmentation masks for inputted medical imaging volumes. In various cases, the training component can implement any suitable training batch sizes, any suitable training termination criteria, or any suitable error, loss, or objective functions.

Similarly, to help cause the sagittally-bisecting surface localization to be accurate, the second deep learning neural network can undergo any suitable type or paradigm of training (e.g., supervised training, unsupervised training, reinforcement learning). Accordingly, in various aspects, the access component can receive, retrieve, or otherwise access a second training dataset, and the training component can train the second deep learning neural network on the second training dataset.

In some instances, the second training dataset can be annotated. In such cases, the second training dataset can include a second set of training medical imaging volumes and a set of ground-truth localizations that respectively correspond to the second set of training medical imaging volumes. A training medical imaging volume can be as described above. In various aspects, a ground-truth localization can be any suitable electronic data having the same format, size, or dimensionality as the sagittally-bisecting surface localization discussed above. Accordingly, a ground-truth localization can indicate, represent, or otherwise identify a planar or curved surface which is known or deemed to sagittally-bisect a spine depicted in a respective training medical imaging volume.

If the second training dataset is annotated, then the training component can, in various aspects, perform supervised training on the second deep learning neural network. Prior to the start of such supervised training, the training component can randomly initialize internal parameters (e.g., weights, biases, convolutional kernels) of the second deep learning neural network.

In various aspects, the training component can select from the second training dataset any suitable training medical imaging volume and any suitable ground-truth localization corresponding to such selected training medical imaging volume. In various instances, the training component can execute the second deep learning neural network on the selected training medical imaging volume, thereby causing the second deep learning neural network to produce some output. For example, the training component can feed the selected training medical imaging volume to an input layer of the second deep learning neural network, the selected training medical imaging volume can complete a forward pass through one or more hidden layers of the second deep learning neural network, and an output layer of the second deep learning neural network can compute the output based on activations generated by the one or more hidden layers. Note that, as mentioned above, the dimensionality of the output can be controlled or otherwise determined by the number of neurons in the output layer (e.g., an output of a desired size can be achieved by adding neurons to or removing neurons from the output layer of the second deep learning neural network). In any case, the output can be considered as the predicted or inferred sagittally-bisecting surface localization that the second deep learning neural network identifies as corresponding to the selected training medical imaging volume. In contrast, the selected ground-truth localization can be considered as the correct or accurate sagittally-bisecting surface localization that is known or deemed to correspond to the selected training medical imaging volume. Note that, if the second deep learning neural network has so far undergone no or little training, then the output can be highly inaccurate (e.g., can be highly different from the selected ground-truth localization). In various aspects, the training component can compute one or more errors or losses (e.g., MAE, MSE, cross-entropy) between the output and the selected ground-truth localization. In various instances, the training component can update the internal parameters of the second deep learning neural network by performing backpropagation (e.g., stochastic gradient descent) driven by the one or more errors or losses.

In various instances, such supervised training procedure can be repeated for each training medical imaging volume in the second training dataset, with the result being that the internal parameters of the second deep learning neural network can become iteratively optimized to accurately localize surfaces that sagittally-bisect spines depicted in inputted medical imaging volumes. In various cases, the training component can implement any suitable training batch sizes, any suitable training termination criteria, or any suitable error, loss, or objective functions.

Accordingly, various embodiments described herein can be considered as a computerized tool that can automatically generate a butterfly-view of an inputted medical imaging volume, where such butterfly-view can illustrate or otherwise visualize surgically-inserted spinal hardware without the clutter or confusion caused by sagittal superimposition.

Various embodiments described herein can be employed to use hardware or software to solve problems that are highly technical in nature (e.g., to facilitate improved spinal hardware rendering), that are not abstract and that cannot be performed as a set of mental acts by a human. Further, some of the processes performed can be performed by a specialized computer (e.g., a deep learning neural network having internal parameters such as convolutional kernels) for carrying out defined tasks related to improved spinal hardware rendering. For example, such defined tasks can include: accessing, by a device operatively coupled to a processor, a medical imaging voxel array depicting a spine of a medical patient; determining, by the device, whether the medical imaging voxel array depicts a set of surgical hardware inserted in the spine of the medical patient; localizing, by the device and in response to a determination that the medical imaging voxel array depicts the set of surgical hardware, a surface that sagittally bisects the spine of the medical patient; and rendering, by the device and on an electronic display, a butterfly-view of the medical imaging voxel array, wherein the butterfly-view is hinged about the localized surface. In various cases, the butterfly-view can comprise a left pane and a right pane, wherein the left pane can depict voxels of the medical imaging voxel array that are leftward of the localized surface and that can depict no voxels of the medical imaging voxel array that are rightward of the localized surface, and wherein the right pane can depict voxels of the medical imaging voxel array that are rightward of the localized surface and that can depict no voxels of the medical imaging voxel array that are leftward of the localized surface.

Such defined tasks are not performed manually by humans. Indeed, neither the human mind nor a human with pen and paper can electronically access a three-dimensional medical image (e.g., an X-ray voxel array, an MRI voxel array, an ultrasound voxel array, a PET voxel array, a CT voxel array) depicting a spine of a medical patient and electronically render, on a computer screen, a butterfly-view of such three-dimensional medical image. Indeed, as described herein, the butterfly-view can be considered as a specific graphical user-interface layout for visualizing surgically-inserted spinal hardware. Simply put, the human mind or a human with pen and paper is not capable of rendering such a specific graphical user-interface layout on a computer screen. Accordingly, a computerized tool that can render a butterfly-view of a three-dimensional voxel array is inherently-computerized and cannot be implemented in any sensible, practical, or reasonable way without computers.

Moreover, various embodiments described herein can integrate into a practical application various teachings relating to improved spinal hardware rendering. As described above, it can be desired to visualize surgically-inserted spinal hardware, so that a medical professional can check whether or not the positions or orientations of such surgically-inserted spinal hardware are proper. Usually, such spinal hardware (e.g., screws, plates) are inserted in a back-to-front direction of a spine of a medical patient, instead of a top-to-bottom direction or a left-to-right direction. Accordingly, a medical professional can check the positions or orientations of such spinal hardware by visually inspecting a sagittal projection of a medical imaging volume that depicts the spine of the medical patient. However, such spinal hardware are also usually grouped as sagittal pairs or sagittal counterparts (e.g., a plate inserted on the left side of the spine, and a corresponding plate inserted on the right side of the spine). Thus, when viewed from the perspective of a sagittal projection, such sagittal pairs or sagittal counterparts can be superimposed on top of each other. Such superimposition can cause the sagittal projection to appear cluttered or confusing, which can adversely affect a medical professional that is attempting to verify the positions or orientations of the surgically-inserted spinal hardware.

Various embodiments described herein can address such technical problem. Specifically, various embodiments described herein can be considered as a computerized tool that can electronically render (e.g., via implementation of deep learning) a butterfly-view of the medical imaging volume. As described herein, the butterfly-view can be considered as the result obtained by: slicing the medical imaging volume along a surface that sagittally-bisects the spine depicted in the medical imaging volume, thereby yielding a left volume and a right volume; and swinging both the left volume and the right volume outward about the sagittally-bisecting surface. In other words, the butterfly-view can include a left pane that illustrates a projection (e.g., a sagittal projection) of only those voxels that are leftward of the sagittally-bisecting surface, and the butterfly-view can include a right pane that illustrates a projection (e.g., a sagittal projection) of only those voxels that are rightward of the sagittally-bisecting surface. Accordingly, for any given sagittal pair of surgically-inserted spinal hardware depicted in the medical imaging volume, such given sagittal pair can be split up between the left pane and the right pane (e.g., half of such sagittal pair can be leftward of the sagittally-bisecting surface, and the remaining half of such sagittal pair can be rightward of the sagittally-bisecting surface). In other words, sagittal projections of such given sagittal pair of surgical hardware can be obtained without superimposing such given sagittal pair on top of each other. That is, the butterfly-view as described herein can be considered as a particular graphical user-interface layout for visualizing surgically-inserted spinal hardware, where such particular graphical user-interface layout can ameliorate the clutter or confusion caused by sagittal superimposition of surgically-inserted spinal hardware. When such clutter or confusion is reduced, a medical professional can be better able to inspect positions or orientations of surgically-inserted spinal hardware (e.g., can perform such inspection more quickly, can perform such inspection more accurately). Accordingly, various embodiments described herein can be considered as an improved surgically-inserted spinal hardware visualization technique. Thus, various embodiments described herein certainly constitute a concrete and tangible technical improvement in the field of medical imaging. Therefore, various embodiments described herein clearly qualify as useful and practical applications of computers.

Furthermore, various embodiments described herein can control real-world tangible devices based on the disclosed teachings. For example, various embodiments described herein can electronically render specific views/projections of real-world medical imaging voxel arrays (e.g., real-world X-ray scans, real-world MRI scans, real-world CT scans) on real-world computer displays.

It should be appreciated that the herein figures and description provide non-limiting examples of various embodiments and are not necessarily drawn to scale.

FIG. 1 illustrates a block diagram of an example, non-limiting system 100 that can facilitate improved spinal hardware rendering in accordance with one or more embodiments described herein. As shown, a spinal hardware rendition system 102 can be electronically integrated, via any suitable wired or wireless electronic connections, with a medical imaging voxel array 104.

In various embodiments, the medical imaging voxel array 104 can exhibit any suitable number or arrangement of voxels. As a non-limiting example, the medical imaging voxel array 104 can be an x-by-y-by-z array of voxels, for any suitable positive integers x, y, and z. Moreover, in various aspects, the medical imaging voxel array 104 can be generated or otherwise captured by any suitable type of medical imaging modality (not shown). As a non-limiting example, the medical imaging voxel array 104 can be generated or otherwise captured by a CT scanner, in which case the medical imaging voxel array 104 can be considered as a three-dimensional CT scanned image. As another non-limiting example, the medical imaging voxel array 104 can be generated or otherwise captured by an MRI scanner, in which case the medical imaging voxel array 104 can be considered as a three-dimensional MRI scanned image. As still another non-limiting example, the medical imaging voxel array 104 can be generated or otherwise captured by a PET scanner, in which case the medical imaging voxel array 104 can be considered as a three-dimensional PET scanned image. As even another non-limiting example, the medical imaging voxel array 104 can be generated or otherwise captured by an X-ray scanner, in which case the medical imaging voxel array 104 can be considered as a three-dimensional X-ray scanned image. As yet another non-limiting example, the medical imaging voxel array 104 can be generated or otherwise captured by an ultrasound scanner, in which case the medical imaging voxel array 104 can be considered as a three-dimensional ultrasound scanned image. In any case, the medical imaging voxel array 104 can have undergone any suitable types of image reconstruction (e.g., filtered backprojection) or image enhancement (e.g., image denoising, brightness/contrast adjustment).

In various aspects, the medical imaging voxel array 104 can depict, show, or otherwise illustrate any suitable portion of a spine 106 of a medical patient. In various instances, the medical imaging voxel array 104 can depict one or more cervical vertebrae of the spine 106. In various other instances, the medical imaging voxel array 104 can depict one or more thoracic vertebrae of the spine 106. In yet other instances, the medical imaging voxel array 104 can depict one or more lumbar vertebrae of the spine 106. In some cases, the medical imaging voxel array 104 can depict any suitable combination of cervical, thoracic, or lumbar vertebrae of the spine 106.

In various aspects, the medical imaging voxel array 104 can depict a set of surgical hardware 108, where the set of surgical hardware 108 can have been mechanically inserted into or on the spine 106. In various instances, the set of surgical hardware 108 can comprise any suitable number of pieces of surgical hardware. In various cases, a piece of surgical hardware can include any suitable piece of metal, plastic, or other substance that can be surgically inserted into the spine 106 or that can be otherwise surgically affixed to the spine 106. As a non-limiting example, a piece of surgical hardware can be a spinal screw that can be drilled into a vertebra of the spine 106. As another non-limiting example, a piece of surgical hardware can be a spinal rod that can be affixed to the spine 106. As even another non-limiting example, a piece of surgical hardware can be a spinal plate that can be attached to the spine 106.

In any case, a medical professional can desire to inspect whether or not the set of surgical hardware 108 are properly positioned or oriented within or otherwise with respect to the spine 106. As described herein, the spinal hardware rendition system 102 can electronically generate a specific visualization layout based on the medical imaging voxel array 104, which specific visualization layout can help to quicken or ease such inspection by the medical professional.

In various embodiments, the spinal hardware rendition system 102 can comprise a processor 110 (e.g., computer processing unit, microprocessor) and a non-transitory computer-readable memory 112 that is operably or operatively or communicatively connected or coupled to the processor 110. The non-transitory computer-readable memory 112 can store computer-executable instructions which, upon execution by the processor 110, can cause the processor 110 or other components of the spinal hardware rendition system 102 (e.g., access component 114, hardware component 116, surface component 118, visualization component 120) to perform one or more acts. In various embodiments, the non-transitory computer-readable memory 112 can store computer-executable components (e.g., access component 114, hardware component 116, surface component 118, visualization component 120), and the processor 110 can execute the computer-executable components.

In various embodiments, the spinal hardware rendition system 102 can comprise an access component 114. In various aspects, the access component 114 can electronically receive or otherwise electronically access the medical imaging voxel array 104. In various instances, the access component 114 can electronically retrieve the medical imaging voxel array 104 from any suitable centralized or decentralized data structures (not shown) or from any suitable centralized or decentralized computing devices (not shown).

For example, the access component 114 can retrieve the medical imaging voxel array 104 from whatever medical imaging device (e.g., CT scanner, MRI scanner, X-ray scanner, ultrasound scanner, PET scanner) generated or captured the medical imaging voxel array 104. In any case, the access component 114 can electronically obtain or access the medical imaging voxel array 104, such that other components of the spinal hardware rendition system 102 can electronically interact with the medical imaging voxel array 104.

In various embodiments, the spinal hardware rendition system 102 can comprise a hardware component 116. In various aspects, as described herein, the hardware component 116 can confirm (e.g., via deep learning) whether the medical imaging voxel array 104 depicts the set of surgical hardware 108.

In various embodiments, the spinal hardware rendition system 102 can comprise a surface component 118. In various instances, as described herein, the surface component 118 can, in response to the hardware component 116 confirming that the medical imaging voxel array 104 depicts the set of surgical hardware 108, localize (e.g., via deep learning) within the medical imaging voxel array a surface that sagittally-bisects the spine 106.

In various embodiments, the spinal hardware rendition system 102 can comprise a visualization component 120. In various cases, as described herein, the visualization component 120 can render a butterfly-view of the medical imaging voxel array 104, based on the surface localized by the surface component 118.

Figure 2:
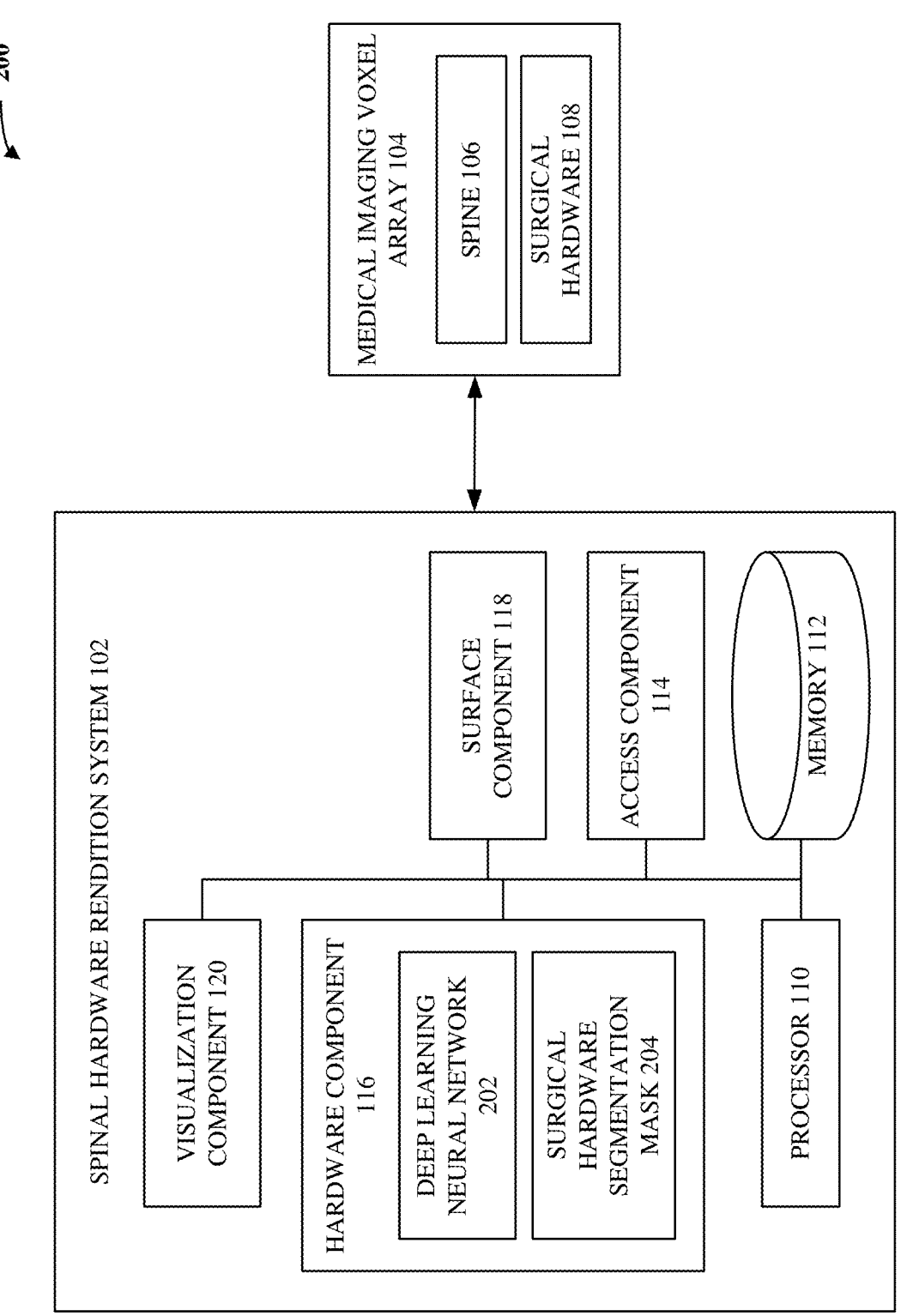
FIG. 2 illustrates a block diagram of an example, non-limiting system including a deep learning neural network and a surgical hardware segmentation mask that facilitates improved spinal hardware rendering in accordance with one or more embodiments described herein.

FIG. 2 illustrates a block diagram of an example, non-limiting system 200 including a deep learning neural network and a surgical hardware segmentation mask that can facilitate improved spinal hardware rendering in accordance with one or more embodiments described herein. As shown, the system 200 can, in some cases, comprise the same components as the system 100, and can further comprise a deep learning neural network 202 and a surgical hardware segmentation mask 204.

In various embodiments, the hardware component 116 can electronically store, electronically maintain, electronically control, or otherwise electronically access the deep learning neural network 202. In various aspects, the deep learning neural network 202 can have or otherwise exhibit any suitable internal architecture. For instance, the deep learning neural network 202 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the hardware component 116 can electronically execute the deep learning neural network 202 on the medical imaging voxel array 104, and such execution can cause the deep learning neural network 202 to produce the surgical hardware segmentation mask 204. Various non-limiting aspects are further described with respect to FIG. 3.

Figure 3:
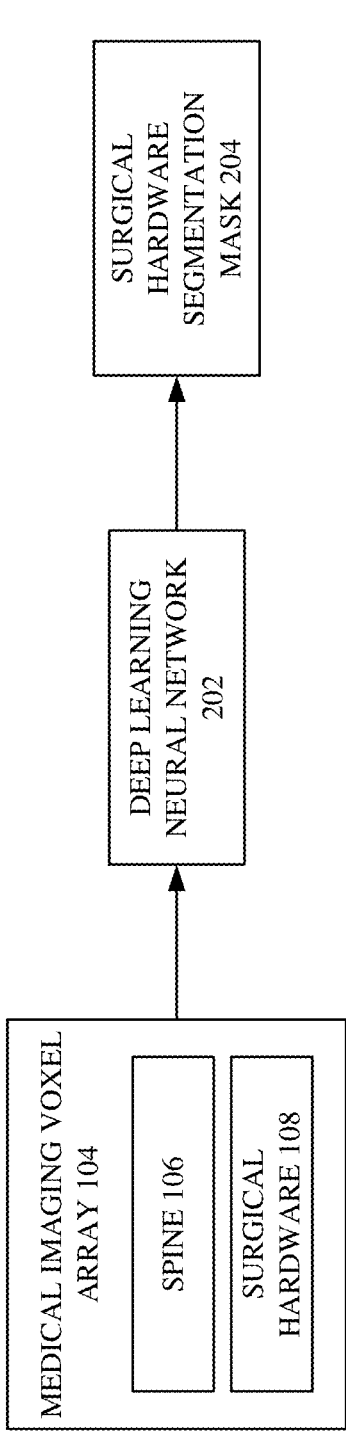
FIG. 3 illustrates an example, non-limiting block diagram showing how a deep learning neural network can generate a surgical hardware segmentation mask in accordance with one or more embodiments described herein.

FIG. 3 illustrates an example, non-limiting block diagram 300 showing how the deep learning neural network 202 can generate the surgical hardware segmentation mask 204 in accordance with one or more embodiments described herein.

As shown, the hardware component 116 can, in various aspects, feed the medical imaging voxel array 104 as input to the deep learning neural network 202. In response, the deep learning neural network 202 can generate the surgical hardware segmentation mask 204. More specifically, the hardware component 116 can provide or otherwise pass the medical imaging voxel array 104 to an input layer of the deep learning neural network 202. In various instances, the medical imaging voxel array 104 can complete a forward pass through one or more hidden layers of the deep learning neural network 202. In various cases, an output layer of the deep learning neural network 202 can compute or otherwise calculate the surgical hardware segmentation mask 204, based on activation maps generated by the one or more hidden layers of the deep learning neural network 202.

In any case, the surgical hardware segmentation mask 204 can be a voxel-wise segmentation mask that indicates which voxels of the medical imaging voxel array 104 belong to any of the set of surgical hardware 108 and which voxels of the medical imaging voxel array 104 do not belong to any of the set of surgical hardware 108. In various aspects, the surgical hardware segmentation mask 204 can exhibit the same format, size, or dimensionality as the medical imaging voxel array 104. Accordingly, since the medical imaging voxel array 104 can be an x-by-y-by-z array of voxels, the surgical hardware segmentation mask 204 can be an x-by-y-by-z array of elements (e.g., array of scalars), where each element of the surgical hardware segmentation mask 204 can indicate to which class a respective voxel of the medical imaging voxel array 104 belongs. In various instances, dichotomous voxel-wise classes can be implemented, such as a surgical hardware class or a background class (e.g., in such case, a voxel can be classified as belonging to the set of surgical hardware 108 or as not belonging to the set of surgical hardware 108). In various other instances, however, multi-chotomous voxel-wise classes can be implemented, such as a screw class, a plate class, a rod class, or a background class (e.g., in such case, a voxel can be classified as belonging to a screw of the set of surgical hardware 108, as belonging to a plate of the set of surgical hardware 108, as belonging to a rod of the surgical hardware 108, or as not belonging to the set of surgical hardware 108). In various aspects, any other suitable types or numbers of voxel-wise classes can be implemented in the surgical hardware segmentation mask 204.

In various cases, the hardware component 116 can analyze the surgical hardware segmentation mask 204, so as to confirm whether or not the medical imaging voxel array 104 depicts the set of surgical hardware 108.

For instance, the hardware component 116 can conclude that the medical imaging voxel array 104 does not depict the set of surgical hardware 108, if the surgical hardware segmentation mask 204 indicates that fewer than any suitable threshold number of voxels of the medical imaging voxel array 104 belong to the set of surgical hardware 108.

In such case, the surface component 118 can refrain from taking any action, and the visualization component 120 can electronically render, on any suitable electronic display (e.g., any suitable computer screen, computer monitor, computer graphical user-interface), an electronic notification stating that the set of surgical hardware 108 were not detected in the medical imaging voxel array 104.

Indeed, as mentioned above, the spinal hardware rendition system 102 can render a specific visualization layout that can help a medical professional to more easily inspect positions or orientations of surgically-inserted spinal hardware. Accordingly, if the spinal hardware rendition system 102 is fed (e.g., accidentally or mistakenly by a technician) a medical imaging volume that does not depict any surgically-inserted spinal hardware, there can be no need to render such specific visualization layout. Accordingly, as described above, the hardware component 116 can confirm or otherwise verify whether the medical imaging voxel array 104 actually depicts the set of surgical hardware 108 based on the surgical hardware segmentation mask 204, and the spinal hardware rendition system 102 can refrain from rendering such specific visualization layout in response to the hardware component 116 concluding that the medical imaging voxel array 104 does not actually depict the set of surgical hardware 108.

On the other hand, the hardware component 116 can conclude that the medical imaging voxel array 104 does depict the set of surgical hardware 108, if the surgical hardware segmentation mask 204 indicates that more than any suitable threshold number of voxels of the medical imaging voxel array 104 belong to the set of surgical hardware 108. In such case, the surface component 118 can initiate various actions, as described below.

Although the herein disclosure mainly describes the deep learning neural network 202 as indicating the intra-image location of the surgical hardware 108 via the surgical hardware segmentation mask 204, this is a mere non-limiting example for case of illustration and explanation. In various cases, the deep learning neural network 202 can instead be configured to produce as output any other suitable electronic data having any suitable format that can indicate, represent, or otherwise convey the intra-image location of the surgical hardware 108. As a non-limiting example, rather than being configured to produce a segmentation mask that indicates the intra-image location of the surgical hardware 108, the deep learning neural network 202 can instead be configured to produce one or more bounding boxes that indicate the intra-image location of the surgical hardware 108. As another non-limiting example, rather than being configured to produce a segmentation mask that indicates the intra-image location of the surgical hardware 108, the deep learning neural network 202 can instead be configured to produce one or more centroidal points that indicate the intra-image location of the surgical hardware 108.

Figure 4:
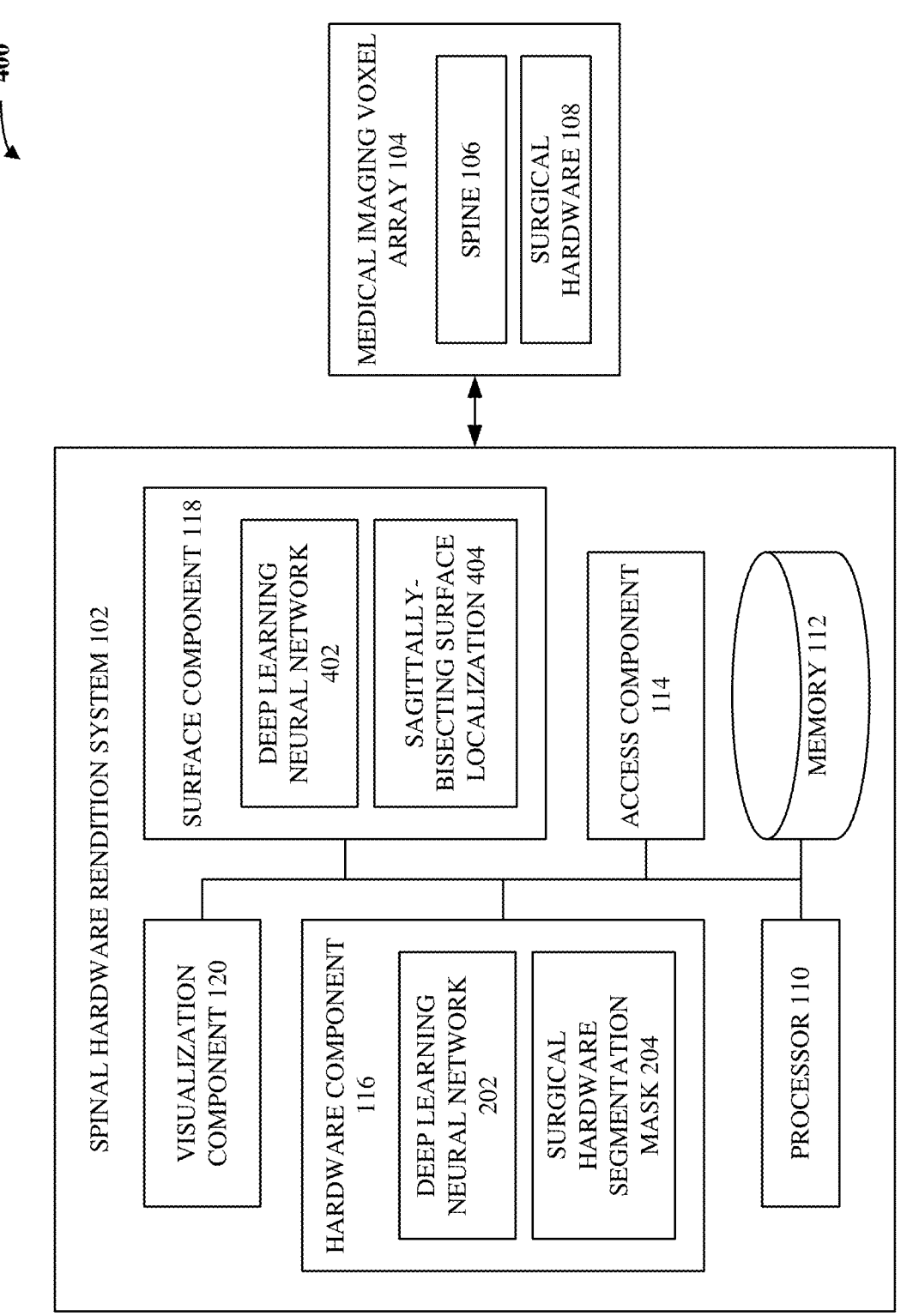
FIG. 4 illustrates a block diagram of an example, non-limiting system including a deep learning neural network and a sagittally-bisecting surface localization that facilitates improved spinal hardware rendering in accordance with one or more embodiments described herein.

FIG. 4 illustrates a block diagram of an example, non-limiting system 400 including a deep learning neural network and a sagittally-bisecting surface localization that can facilitate improved spinal hardware rendering in accordance with one or more embodiments described herein. As shown, the system 400 can, in some cases, comprise the same components as the system 200, and can further comprise a deep learning neural network 402 and a sagittally-bisecting surface localization 404.

In various embodiments, the surface component 118 can electronically store, electronically maintain, electronically control, or otherwise electronically access the deep learning neural network 402. In various aspects, the deep learning neural network 402 can have or otherwise exhibit any suitable internal architecture. For instance, the deep learning neural network 402 can have an input layer, one or more hidden layers, and an output layer. In various cases, any of such layers can be coupled together by any suitable interneuron connections or interlayer connections (e.g., forward connections, skip connections, recurrent connections). Furthermore, in various aspects, any of such layers can be any suitable types of neural network layers having any suitable learnable or trainable internal parameters (e.g., any of such input layer, one or more hidden layers, or output layer can be convolutional layers having trainable convolutional kernels, dense layers having trainable weight matrices or bias values, or batch normalization layers having trainable shift factors or scale factors). Further still, in various cases, any of such layers can be any suitable types of neural network layers having any suitable fixed or non-trainable internal parameters (e.g., any of such input layer, one or more hidden layers, or output layer can be non-linearity layers, padding layers, pooling layers, or concatenation layers).

In various aspects, and in response to the hardware component 116 confirming that the medical imaging voxel array 104 does depict the set of surgical hardware 108, the surface component 118 can electronically execute the deep learning neural network 402 on the medical imaging voxel array 104. In various instances, such execution can cause the deep learning neural network 402 to produce the sagittally-bisecting surface localization 404. Various non-limiting aspects are further described with respect to FIG. 5.

FIG. 5 illustrates an example, non-limiting block diagram 500 showing how the deep learning neural network 402 can generate the sagittally-bisecting surface localization 404 in accordance with one or more embodiments described herein.

As shown, the surface component 118 can, in various aspects, feed the medical imaging voxel array 104 as input to the deep learning neural network 402. In response, the deep learning neural network 402 can generate the sagittally-bisecting surface localization 404. In particular, the surface component 118 can provide or otherwise pass the medical imaging voxel array 104 to an input layer of the deep learning neural network 402. In various aspects, the medical imaging voxel array 104 can complete a forward pass through one or more hidden layers of the deep learning neural network 402. In various instances, an output layer of the deep learning neural network 402 can compute or otherwise calculate the sagittally-bisecting surface localization 404, based on activation maps generated by the one or more hidden layers of the deep learning neural network 402.

In various aspects, the sagittally-bisecting surface localization 404 can be any suitable electronic data that indicates, represents, or otherwise identifies a planar or curve surface within the medical imaging voxel array 104, where such planar or curved surface can sagittally-bisect the spine 106. In other words, the planar or curved surface can be considered as separating or dividing the spine 106 into a left spinal side and a right spinal side. In some cases, the planar or curved surface can separate or divide the spine 106 into two equal portions (e.g., the left spinal side can be equal to or otherwise symmetric with the right spinal side). However, in other cases, the planar or curved surface can separate or divide the spine 106 into two unequal portions (e.g., the left spinal side can be unequal to or otherwise not symmetric with the right spinal side). In any case, such planar or curved surface can be referred to as sagittally-bisecting the spine 106.

In various aspects, the sagittally-bisecting surface localization 404 can exhibit any suitable format, size, or dimensionality. As a non-limiting example, the sagittally-bisecting surface localization 404 can be any suitable number of parameters that geometrically define (e.g., in Cartesian space) the planar or curved surface that sagittally-bisects the spine 106. For instance, the sagittally-bisecting surface localization 404 can include one or more parameters that define or indicate how the planar or curved surface varies along an x-axis of a Cartesian coordinate system applied to the medical imaging voxel array 104, one or more parameters that define or indicate how the planar or curved surface varies along a y-axis of the Cartesian coordinate system applied to the medical imaging voxel array 104, or one or more parameters that define or indicate how the planar or curved surface varies along a z-axis of the Cartesian coordinate system applied to the medical imaging voxel array 104.

As another non-limiting example, the sagittally-bisecting surface localization 404 can be a voxel-wise segmentation mask that indicates which voxels of the medical imaging voxel array 104 belong to the planar or curved surface that sagittally-bisects the spine 106 and which voxels of the medical imaging voxel array 104 do not belong to such planar or curved surface. In such case, the sagittally-bisecting surface localization 404 can exhibit the same format, size, or dimensionality as the medical imaging voxel array 104. That is, since the medical imaging voxel array 104 can be an x-by-y-by-z array of voxels, the sagittally-bisecting surface localization 404 can be an x-by-y-by-z array of elements (e.g., array of scalars), where each element of the sagittally-bisecting surface localization 404 can indicate to which class a respective voxel of the medical imaging voxel array 104 belongs. In various instances, dichotomous voxel-wise classes can be implemented, such as a sagittally-bisecting surface class or a background class (e.g., in such case, a voxel can be classified as belonging to the planar or curved surface that sagittally-bisects the spine 106 or as not belonging to such planar or curved surface).

To help clarify various aspects discussed above, consider FIGS. 6-7.

Figure 6:
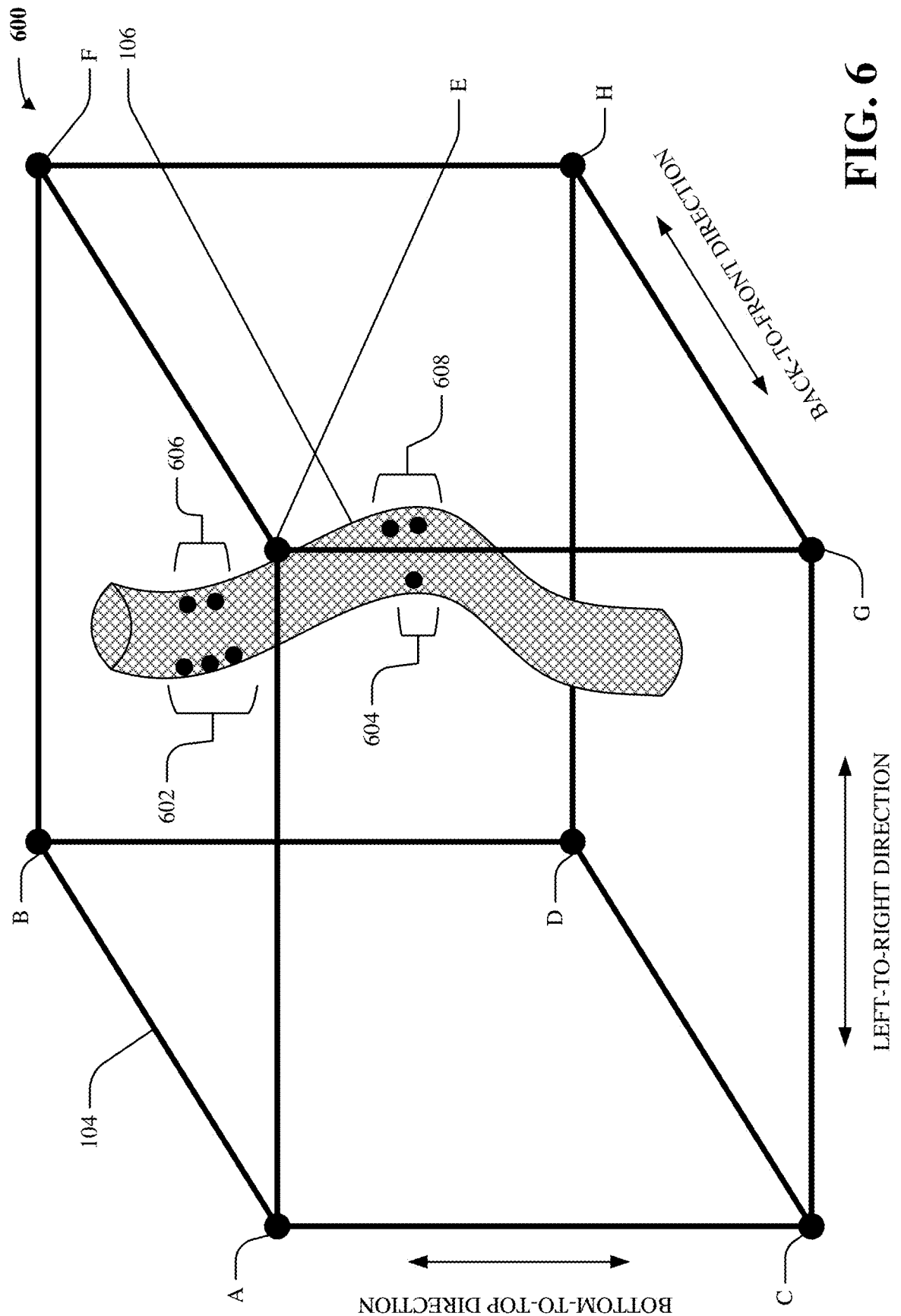
FIGS. 6-7 illustrate example, non-limiting block diagrams pertaining to a sagittally-bisecting surface in accordance with one or more embodiments described herein.
Figure 7:
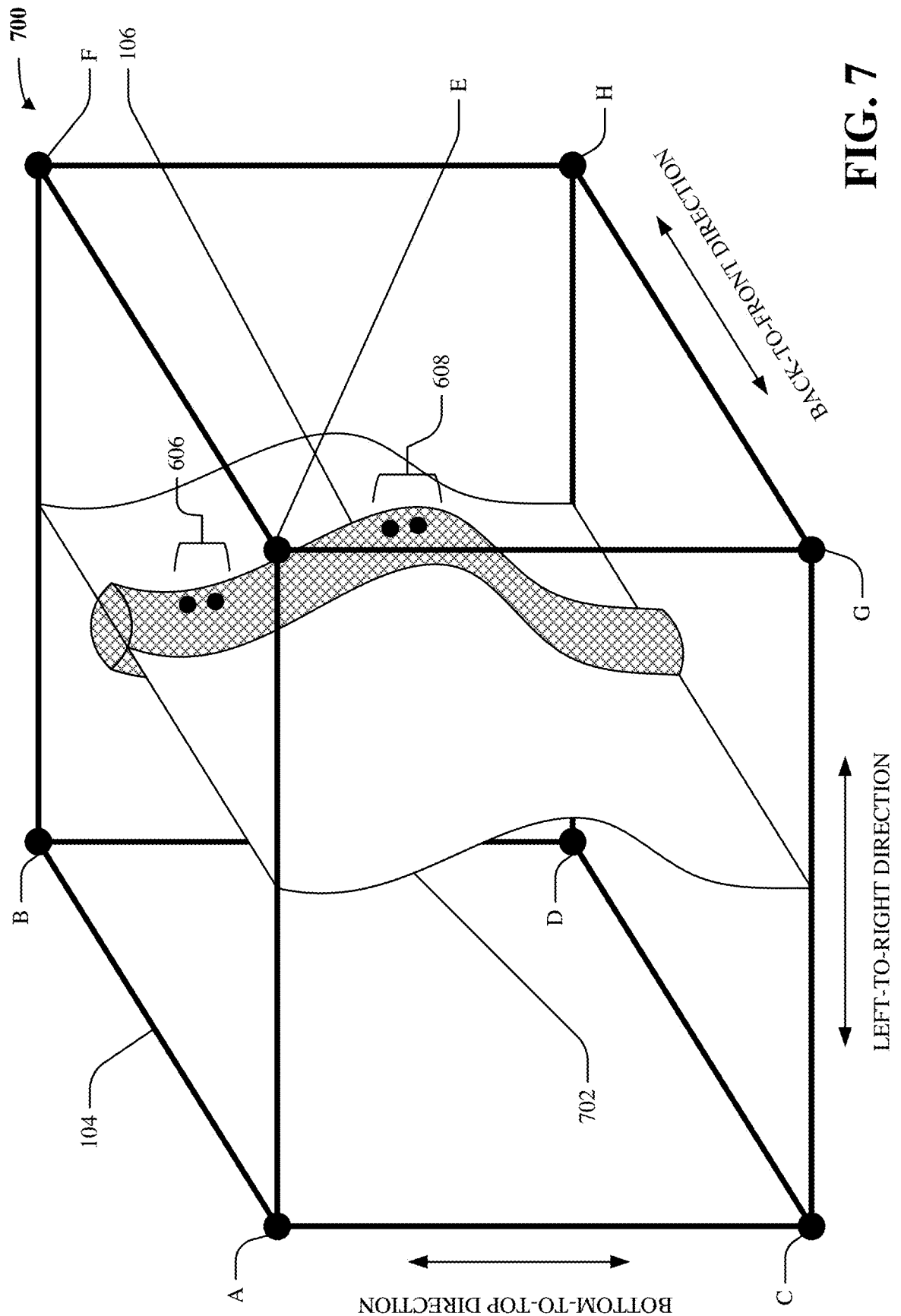

FIGS. 6-7 illustrate example, non-limiting block diagrams 600 and 700 pertaining to a sagittally-bisecting surface in accordance with one or more embodiments described herein. In other words, FIGS. 6-7 depict non-limiting example embodiments of the medical imaging voxel array 104, of the spine 106, and of the planar or curved surface that is indicated or otherwise specified by the sagittally-bisecting surface localization 404.

First, consider FIG. 6. As shown, the medical imaging voxel array 104 can, in various aspects, be considered as forming a cuboid having eight corners: a corner A, a corner B, a corner C, a corner D, a corner E, a corner F, a corner G, and a corner H. Note that, although FIG. 6 depicts the medical imaging voxel array 104 as being a cuboid, this is a mere non-limiting example for ease of illustration. In various other aspects, the medical imaging voxel array 104 can form any other suitable three-dimensional shape.

As also shown, a first direction or axis of the medical imaging voxel array 104 can be considered as being a bottom-to-top direction, a second direction or axis of the medical imaging voxel array 104 can be considered as being a left-to-right direction, and a third direction or axis of the medical imaging voxel array 104 can be considered as being a back-to-front direction. In particular, as shown, the bottom-to-top direction can run orthogonally to a plane CDHG and to a plane ABFE of the medical imaging voxel array 104. Similarly, as shown, the left-to-right direction can run orthogonally to a plane EFHG and a plane ABDC of the medical imaging voxel array 104. Likewise, as shown, the back-to-front direction can run orthogonally to a plane ACGE and to a plane BDHF of the medical imaging voxel array 104. Although FIG. 6 illustrates the bottom-to-top, left-to-right, and back-to-front directions as being aligned with the edges or planes of the medical imaging voxel array 104, this is a mere non-limiting example for case of illustration. Indeed, in various cases, such directions can be oblique to the edges or planes of the medical imaging voxel array 104.

In any case, as shown, the medical imaging voxel array 104 can illustrate or otherwise depict the spine 106. Moreover, in various aspects, the medical imaging voxel array 104 can illustrate or otherwise depict various pieces of surgically-inserted spinal hardware (e.g., various of the set of surgical hardware 108) within the spine 106. As a non-limiting example, the medical imaging voxel array 104 can illustrate or otherwise depict one or more spinal screws 602 as being inserted into an upper-left portion of the spine 106. In the non-limiting example shown in FIG. 6, the one or more spinal screws 602 can include three screws. As another non-limiting example, the medical imaging voxel array 104 can illustrate or otherwise depict one or more spinal screws 604 as being inserted into a middle-left portion of the spine 106. In the non-limiting example shown in FIG. 6, the one or more spinal screws 604 can include one screw. As even another non-limiting example, the medical imaging voxel array 104 can illustrate or otherwise depict one or more spinal screws 606 as being inserted into an upper-right portion of the spine 106. In the non-limiting example shown in FIG. 6, the one or more spinal screws 606 can include two screws. As yet another non-limiting example, the medical imaging voxel array 104 can illustrate or otherwise depict one or more spinal screws 608 as being inserted into a middle-right portion of the spine 106. In the non-limiting example shown in FIG. 6, the one or more spinal screws 608 can include two screws.

Now, consider FIG. 7. As shown, there can be a surface 702 that can run through the spine 106 in the back-to-front direction and in the bottom-to-top direction, thereby separating or dividing the spine 106 into a left spinal portion (e.g., leftward of the surface 702) and a right spinal portion (e.g., rightward of the surface 702). In other words, the surface 702 can be considered as sagittally-bisecting the spine 106. In various aspects, the surface 702 can be considered as a non-limiting example of the planar or curved surface specified or otherwise indicated by the sagittally-bisecting surface localization 404. Note that, in the non-limiting example shown in FIG. 7, the one or more spinal screws 606 and the one or more spinal screws 608 can be located rightward of the surface 702, whereas the one or more spinal screws 602 and the one or more spinal screws 604 can be located leftward of the surface 702.

Note that, in various aspects, the surface 702 can follow the curvature of the spine 106. In particular, as shown in the non-limiting examples of FIGS. 6-7, the spine 106 can be curved in the left-to-right direction (e.g., in the real-world, such curve can be indicative of scoliosis). Because the spine 106 can be curved in the left-to-right direction, the surface 702 can likewise be curved in the left-to-right direction, since the surface 702 sagittally-bisects the spine 106. However, this is a mere non-limiting example for purposes of illustration. In various other cases, the spine 106 can be not curved in the left-to-right direction (e.g., a healthy spine without scoliosis would not be curved in the left-to-right direction). In such case, the surface 702 would likewise not be curved in the left-to-right direction. Indeed, in such case where no left-to-right spinal curvature is present, the surface 702 could be considered as a sagittal plane of the medical patient.

In any case, the deep learning neural network 402 can identify or otherwise localize the planar or curved surface that sagittally-bisects the spine 106 (e.g., can locate the surface 702).

Figure 8:
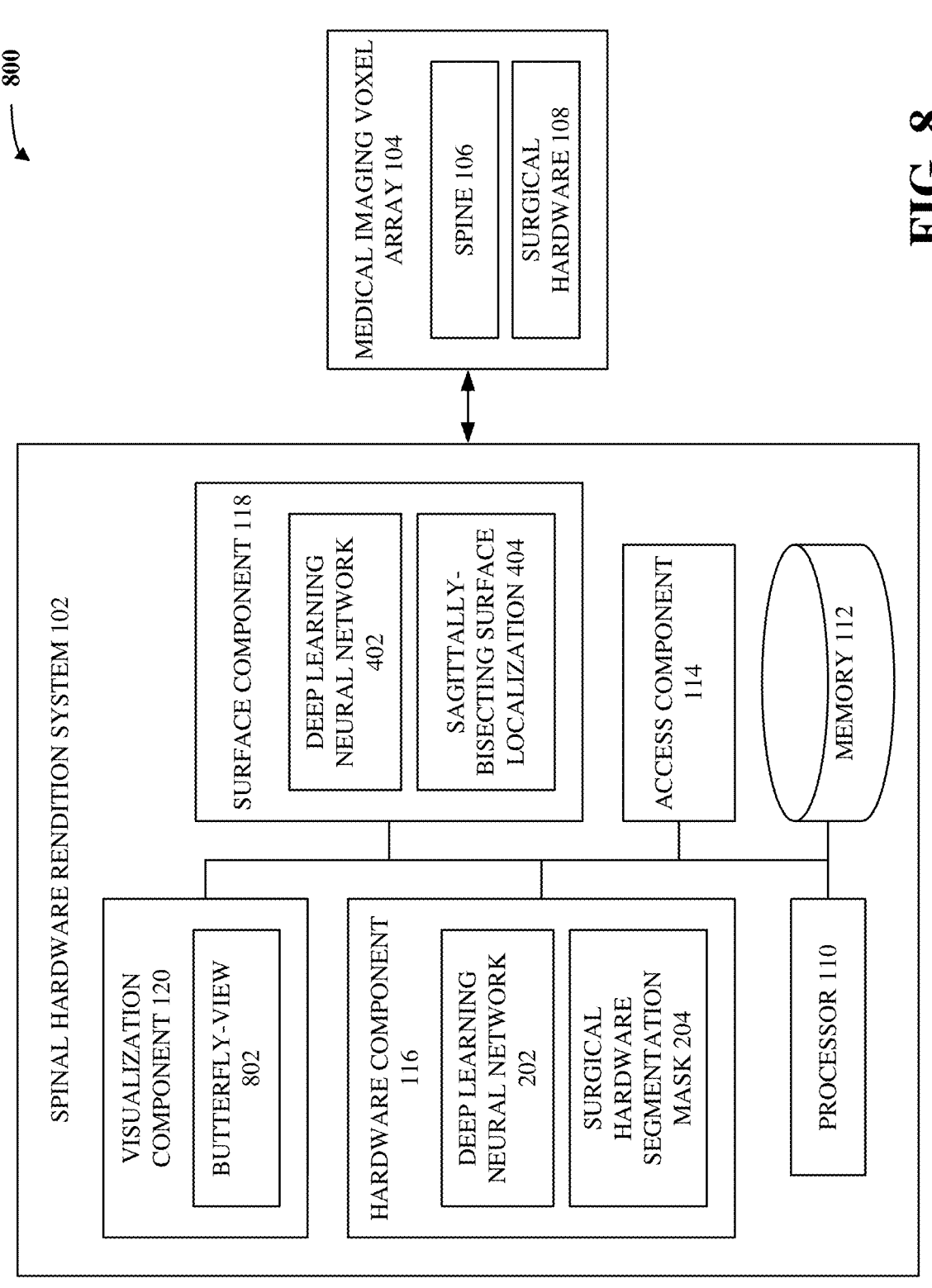
FIG. 8 illustrates a block diagram of an example, non-limiting system including a butterfly-view that facilitates improved spinal hardware rendering in accordance with one or more embodiments described herein.

FIG. 8 illustrates a block diagram of an example, non-limiting system 800 including a butterfly-view that can facilitate improved spinal hardware rendering in accordance with one or more embodiments described herein. As shown, the system 800 can, in some cases, comprise the same components as the system 400, and can further comprise a butterfly-view 802.

In various embodiments, the visualization component 120 can electronically render the butterfly-view 802 on any suitable electronic display (e.g., on any suitable computer screen, computer monitor, or computer graphical user-interface), based on the sagittally-bisecting surface localization 404. In various aspects, the butterfly-view 802 can be considered as a specific visualization layout of the medical imaging voxel array 104, where such specific visualization layout is centered or otherwise hinged about the planar or curved surface that sagittally-bisects the spine 106, and where such specific visualization layout can avoid superimposing sagittal-pairs of the set of surgical hardware 108 on top of each other. Various non-limiting aspects are described with respect to FIG. 9.

Figure 9:
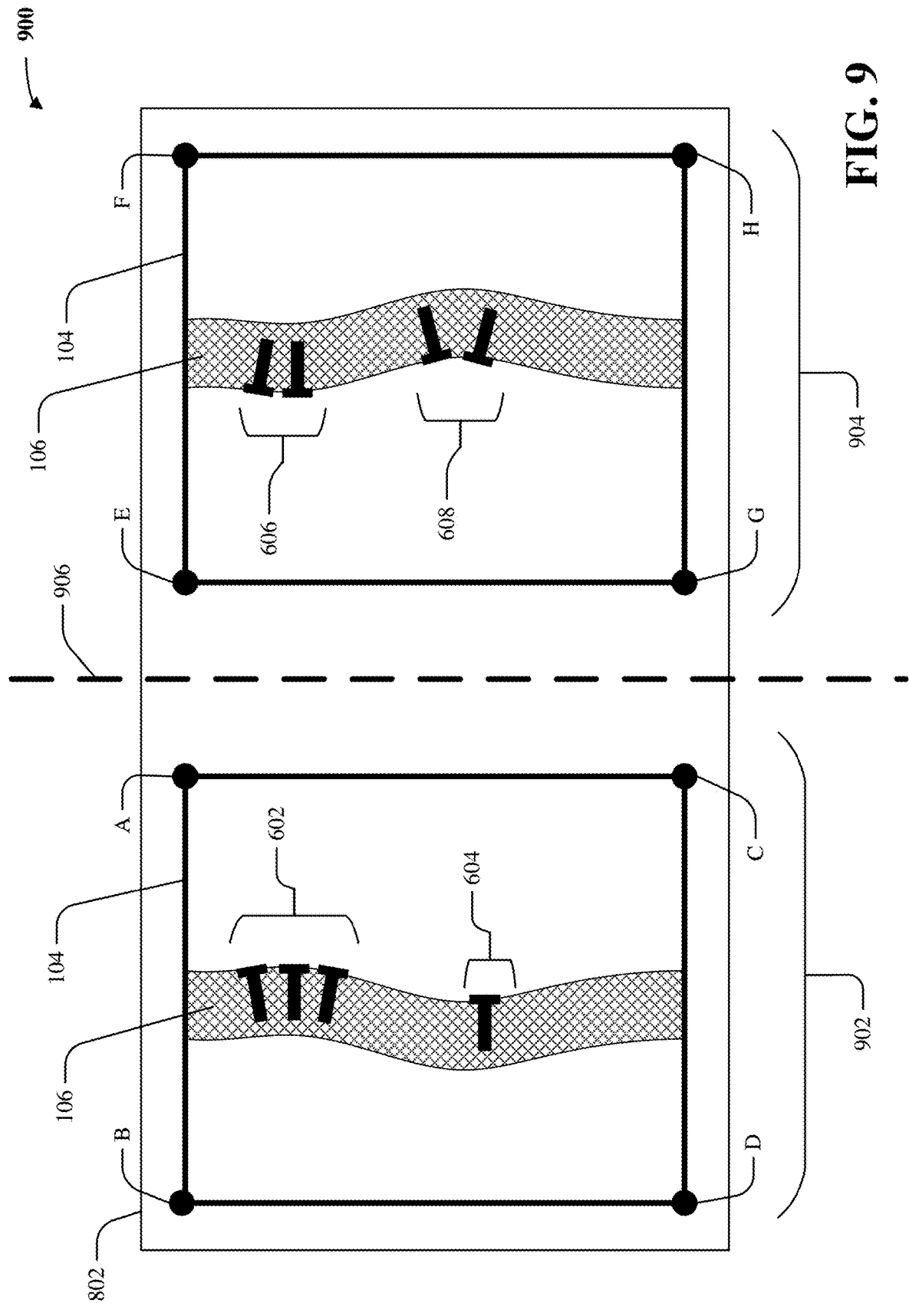
FIG. 9 illustrates an example, non-limiting block diagram showing a butterfly-view in accordance with one or more embodiments described herein.

FIG. 9 illustrates a block diagram 900 showing a non-limiting example of the butterfly-view 802 in accordance with one or more embodiments described herein. In particular, FIG. 9 can be considered as illustrating a non-limiting example embodiment of the butterfly-view 802 which can correspond to the non-limiting example embodiment of the medical imaging voxel array 104 shown in FIGS. 6-7.

As shown, the butterfly-view 802 can comprise a left windowpane 902 and a right windowpane 904. In various aspects, the left windowpane 902 can illustrate, depict, or otherwise visually show any suitable projection, perspective, or view of whatever portion of the medical imaging voxel array 104 is located leftward of the surface 702. In other words, the left windowpane 902 can depict any suitable projection of the voxels of the medical imaging voxel array 104 that are located between the surface 702 and the plane ABDC. Accordingly, the left windowpane 902 can illustrate whatever portion of the spine 106 is leftward of the surface 702. Furthermore, the left windowpane 902 can illustrate whatever pieces of the set of surgical hardware 108 are located leftward of the surface 702. As mentioned above with respect to FIGS. 6-7, the one or more spinal screws 602 and the one or more spinal screws 604 can be located leftward of the surface 702. Thus, the one or more spinal screws 602 and the one or more spinal screws 604 can be depicted in the left windowpane 902.

As shown in FIG. 9, the left windowpane 902 can, in various cases, depict a sagittal projection of the voxels that are located leftward of the surface 702. In various aspects, such sagittal projection shown in the left windowpane 902 can be rendered via any suitable projection technique. As a non-limiting example, such sagittal projection shown in the left windowpane 902 can be rendered via an MIP projection technique. As another non-limiting example, such sagittal projection shown in the left windowpane 902 can be rendered via a transparent VR projection technique.

In any case, the left windowpane 902 can refrain from depicting any voxels of the medical imaging voxel array 104 that are rightward of the surface 702. In other words, the left windowpane 902 can refrain from illustrating any voxels that are located between the surface 702 and the plane EFHG. Accordingly, because the one or more spinal screws 606 and the one or more spinal screws 608 can be located rightward of the surface 702, the one or more spinal screws 606 and the one or more spinal screws 608 can be not depicted or illustrated in the left windowpane 902.

In contrast, the right windowpane 904 can illustrate, depict, or otherwise visually show any suitable projection, perspective, or view of whatever portion of the medical imaging voxel array 104 is located rightward of the surface 702. In other words, the right windowpane 904 can depict any suitable projection of the voxels of the medical imaging voxel array 104 that are located between the surface 702 and the plane EFHG. Accordingly, the right windowpane 904 can illustrate whatever portion of the spine 106 is rightward of the surface 702. Furthermore, the right windowpane 904 can illustrate whatever pieces of the set of surgical hardware 108 are located rightward of the surface 702. As mentioned above with respect to FIGS. 6-7, the one or more spinal screws 606 and the one or more spinal screws 608 can be located rightward of the surface 702. Thus, the one or more spinal screws 606 and the one or more spinal screws 608 can be depicted in the right windowpane 904.

As shown in FIG. 9, the right windowpane 904 can, in various cases, depict a sagittal projection of the voxels that are located rightward of the surface 702. In various aspects, and just as above, such sagittal projection shown in the right windowpane 904 can be rendered via any suitable projection techniques, such as an MIP projection technique or a transparent VR projection technique.

In any case, the right windowpane 904 can refrain from depicting any voxels of the medical imaging voxel array 104 that are leftward of the surface 702. In other words, the right windowpane 904 can refrain from illustrating any voxels that are located between the surface 702 and the plane ABDC. Accordingly, because the one or more spinal screws 602 and the one or more spinal screws 604 can be located leftward of the surface 702, the one or more spinal screws 602 and the one or more spinal screws 604 can be not depicted or illustrated in the left windowpane 902.

Note that, in various aspects, the butterfly-view 802 can be considered as the result that would be obtained if the medical imaging voxel array 104 were split into two sub-voxel-arrays along the surface 702, and the two sub-voxel-arrays were folded, hinged, swiveled, or swung outwardly open (like the wings of a butterfly or the covers of a book) about the surface 702. Conversely, if the butterfly-view 802 were folded in half about an axis 906 that is in between the left windowpane 902 and the right windowpane 904, the result of such folding could be considered as the medical imaging voxel array 104.

Note that, as shown in FIG. 6, the one or more spinal screws 602 and the one or more spinal screws 606 can be considered as being located at about the same elevation as each other within the spine 106. In other words, the one or more spinal screws 602 can be considered as being sagittally-paired with the one or more spinal screws 606. Accordingly, if a traditional sagittal projection of the medical imaging voxel array 104 were rendered, such traditional sagittal projection would superimpose the one or more spinal screws 602 over top of the one or more spinal screws 606. Such a traditional sagittal projection would appear cluttered and confusing, and it would thus be difficult for a medical professional to visually inspect such sagittal projection to check the positions or orientations of the one or more spinal screws 602 and the one or more spinal screws

606. In stark contrast, however, the butterfly-view 802 can depict, in the left windowpane 902, a sagittal projection of the one or more spinal screws 602 without superimposition of the one or more spinal screws 606, and the butterfly-view can also depict, in the right windowpane 904, a sagittal projection of the one or more spinal screws 606 without superimposition of the one or more spinal screws 602. Accordingly, a medical professional can more easily visually inspect the positions or orientations of the one or more spinal screws 602 and the one or more spinal screws 606 by using the butterfly-view 802 instead of a traditional sagittal projection of the medical imaging voxel array 104.

Similarly, note that, as shown in FIG. 6, the one or more spinal screws 604 and the one or more spinal screws 608 can be considered as being located at about the same elevation as each other within the spine 106. In other words, the one or more spinal screws 604 can be considered as being sagittally-paired with the one or more spinal screws 608. Accordingly, if a traditional sagittal projection of the medical imaging voxel array 104 were rendered, such traditional sagittal projection would superimpose the one or more spinal screws 604 over top of the one or more spinal screws 608. Just like above, such a traditional sagittal projection would appear cluttered and confusing, and it would thus be difficult for a medical professional to visually inspect such sagittal projection to check the positions or orientations of the one or more spinal screws 604 and the one or more spinal screws 608. In stark contrast, however, the butterfly-view 802 can depict, in the left windowpane 902, a sagittal projection of the one or more spinal screws 604 without superimposition of the one or more spinal screws 608, and the butterfly-view can also depict, in the right windowpane 904, a sagittal projection of the one or more spinal screws 608 without superimposition of the one or more spinal screws 604. Accordingly, a medical professional can more easily visually inspect the positions or orientations of the one or more spinal screws 604 and the one or more spinal screws 608 by using the butterfly-view 802 instead of a traditional sagittal projection of the medical imaging voxel array 104.

Although FIG. 9 illustrates the left windowpane 902 as depicting a sagittal projection of the voxels that are leftward of the surface 702, this is a mere non-limiting example for case of illustration. In various aspects, the left windowpane 902 can depict any other suitable projection (e.g., coronal projection, axial projection, oblique projection) of the voxels that are leftward of the surface 702. Indeed, in some cases, the projection shown in the left windowpane 902 can be controllably rotatable according to any suitable user-input provided by a technician or by a medical professional (e.g., touchscreen input, voice input, keyboard input, mouse input).

Likewise, although FIG. 9 illustrates the right windowpane 904 as depicting a sagittal projection of the voxels that are rightward of the surface 702, this is a mere non-limiting example for ease of illustration. In various aspects, the right windowpane 904 can depict any other suitable projection (e.g., coronal projection, axial projection, oblique projection) of the voxels that are rightward of the surface 702. Indeed, in some cases, the projection shown in the right windowpane 904 can be controllably rotatable according to any suitable user-input provided by a technician or by a medical professional (e.g., touchscreen input, voice input, keyboard input, mouse input).

FIGS. 10-11 illustrate non-limiting examples 1000 and 1100 of butterfly-views in accordance with one or more embodiments described herein.

First, consider FIG. 10. As shown, FIG. 10 illustrates a sagittal projection 1002 of a three-dimensional medical image showing six separate screws surgically-inserted into a spine. In particular, three screws can be surgically-inserted into the left side of the spine, and the other three screws can be surgically inserted into the right side of the spine. As can be seen, the sagittal projection 1002 can be considered as cluttered or confusing. After all, the sagittal projection 1002 superimposes the three rightward screws over top of the three leftward screws. As a result, it can be difficult to visually inspect the positions or orientations of the six screws.

As also shown, FIG. 10 illustrates a butterfly-view 1004 that was generated as described herein for the three-dimensional medical image showing the six separate screws surgically-inserted into the spine. As can be seen, a left side of the butterfly-view 1004 can depict a sagittal projection of only the voxels that are leftward of whatever surface sagittally-bisects the spine, and so the left side of the butterfly-view 1004 can depict the three leftward screws without superimposition of the three rightward screws. Similarly, a right side of the butterfly-view 1004 can depict a sagittal projection of only the voxels that are rightward of the surface that sagittally-bisects the spine, and so the right side of the butterfly-view 1004 can depict the three rightward screws without superimposition of the three leftward screws. In any case, the butterfly-view 1004 can be considered as less cluttered and less confusing than the sagittal projection 1002. Thus, a medical professional can more easily inspect the positions or orientations of the six screws by examining the butterfly-view 1004 rather than the sagittal projection 1002.

Next, consider FIG. 11. As shown, FIG. 11 illustrates a sagittal projection 1102 of a three-dimensional medical image showing eight separate screws surgically-inserted into a spine. In particular, four screws can be surgically-inserted into the left side of the spine, and the other four screws can be surgically inserted into the right side of the spine. As can be seen, the sagittal projection 1102 can be considered as cluttered or confusing. After all, the sagittal projection 1102 superimposes the four rightward screws over top of the four leftward screws. As a result, it can be difficult to visually inspect the positions or orientations of the eight screws.

As also shown, FIG. 11 illustrates a butterfly-view 1104 that was generated as described herein for the three-dimensional medical image showing the eight separate screws surgically-inserted into the spine. As can be seen, a left side of the butterfly-view 1104 can depict a sagittal projection of only the voxels that are leftward of whatever surface sagittally-bisects the spine, and so the left side of the butterfly-view 1104 can depict the four leftward screws without superimposition of the four rightward screws. Similarly, a right side of the butterfly-view 1104 can depict a sagittal projection of only the voxels that are rightward of the surface that sagittally-bisects the spine, and so the right side of the butterfly-view 1104 can depict the four rightward screws without superimposition of the four leftward screws. In any case, the butterfly-view 1104 can be considered as less cluttered and less confusing than the sagittal projection 1102. Therefore, a medical professional can more easily inspect the positions or orientations of the eight screws by examining the butterfly-view 1104 rather than the sagittal projection 1102.

Note that, as shown in FIG. 11, the tip of the third-from-the-top rightward screw can be missing in the right side of the butterfly-view 1104 and can be illustrated in the left side of the butterfly-view 1104. This can indicate that the third-from-the-top rightward screw crosses through whatever surface sagittally-bisects the spine, such that the tip of such screw is located leftward of the sagittally-bisecting surface, and such that the distal end of such screw is located rightward of the sagittally-bisecting surface. Regardless of such cross-over, the butterfly-view 1104 is still clearly less cluttered and less confusing than the sagittal projection 1102.

In any case, the visualization component 120 can electronically render, on any suitable electronic display, the butterfly-view 802. Accordingly, a medical professional can visually inspect the butterfly-view 802, so as to check the intra-spinal positions or orientations of the set of surgical hardware 108.

Although the left windowpane 902 and the right windowpane 904 are primarily described herein as respectively depicting the voxels that are leftward of the sagittally-bisecting surface and the voxels that are rightward of the sagittally-bisecting surface, this is a mere non-limiting example for case of explanation and illustration. Instead, in various cases, the left windowpane 902 can depict any suitable projection of only the voxels that are located rightward of the sagittally-bisecting surface, and the right windowpane 904 can correspondingly depict any suitable projection of only the voxels that are located leftward of the sagittally-bisecting surface.

To help ensure that the surgical hardware segmentation mask 204 is accurate, the deep learning neural network 202 can first undergo training. Likewise, to help ensure that the sagittally-bisecting surface localization 404 is accurate, the deep learning neural network 402 can first undergo training. Non-limiting example aspects of such training are described with respect to FIGS. 12-16.

Figure 12:
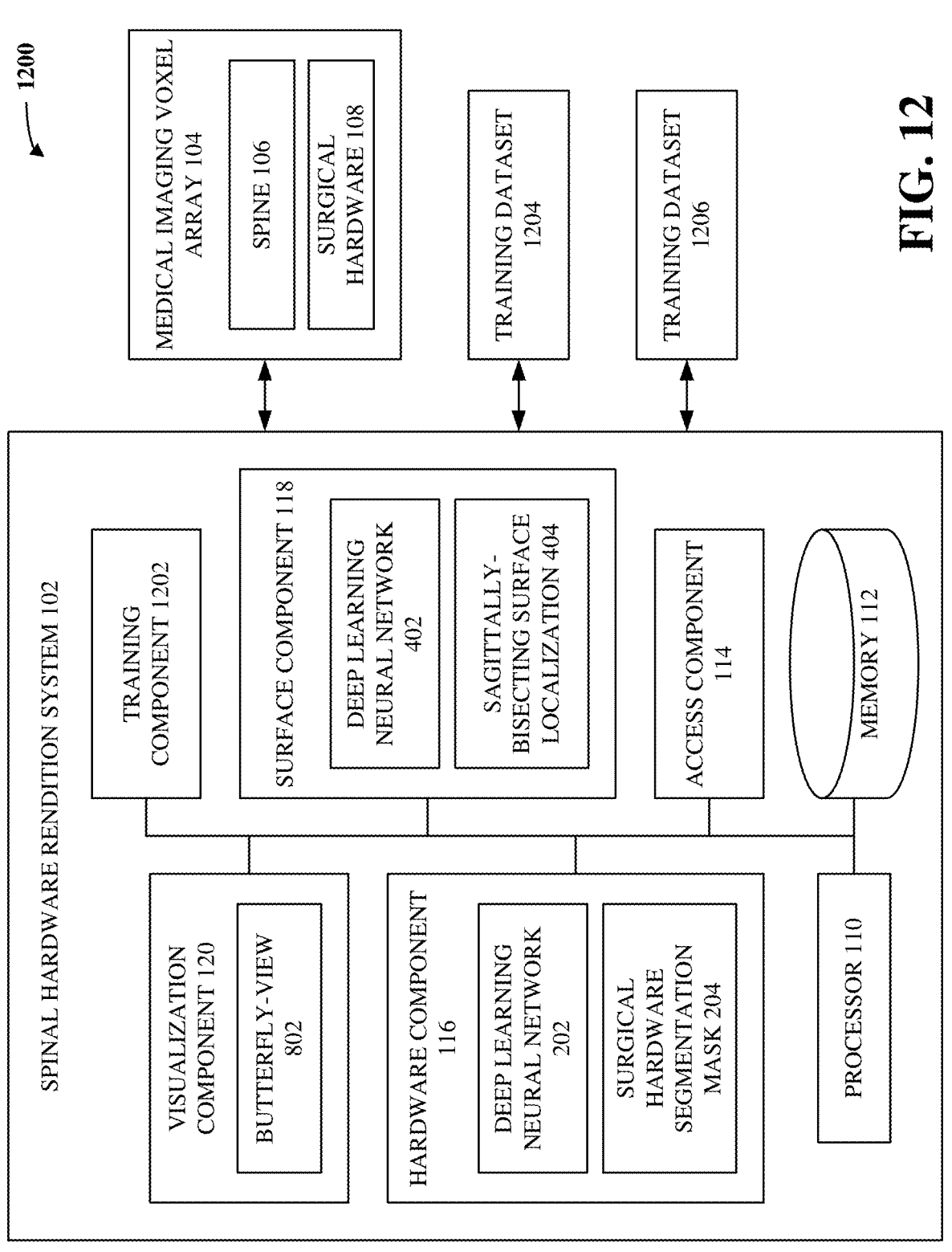
FIG. 12 illustrates a block diagram of an example, non-limiting system including a training component and various training datasets that facilitates improved spinal hardware rendering in accordance with one or more embodiments described herein.

FIG. 12 illustrates a block diagram of an example, non-limiting system 1200 including a training component and various training datasets that can facilitate improved spinal hardware rendering in accordance with one or more embodiments described herein. As shown, the system 1200 can, in some cases, comprise the same components as the system 800, and can further comprise a training component 1202, a training dataset 1204, or a training dataset 1206.

In various embodiments, the access component 114 can electronically receive, retrieve, obtain, or otherwise access, from any suitable source, the training dataset 1204. In various aspects, the training component 1202 can train the deep learning neural network 202 based on the training dataset 1204. In some cases, the training dataset 1204 can be annotated, and so the training component 1202 can perform supervised training on the deep learning neural network 202, as described with respect to FIGS. 13-14.

Similarly, the access component 114 can electronically receive, retrieve, obtain, or otherwise access, from any suitable source, the training dataset 1206. In various aspects, the training component 1202 can train the deep learning neural network 402 based on the training dataset 1206. In some cases, the training dataset 1206 can be annotated, and so the training component 1202 can perform supervised training on the deep learning neural network 402, as described with respect to FIGS. 15-16.

Figure 13:
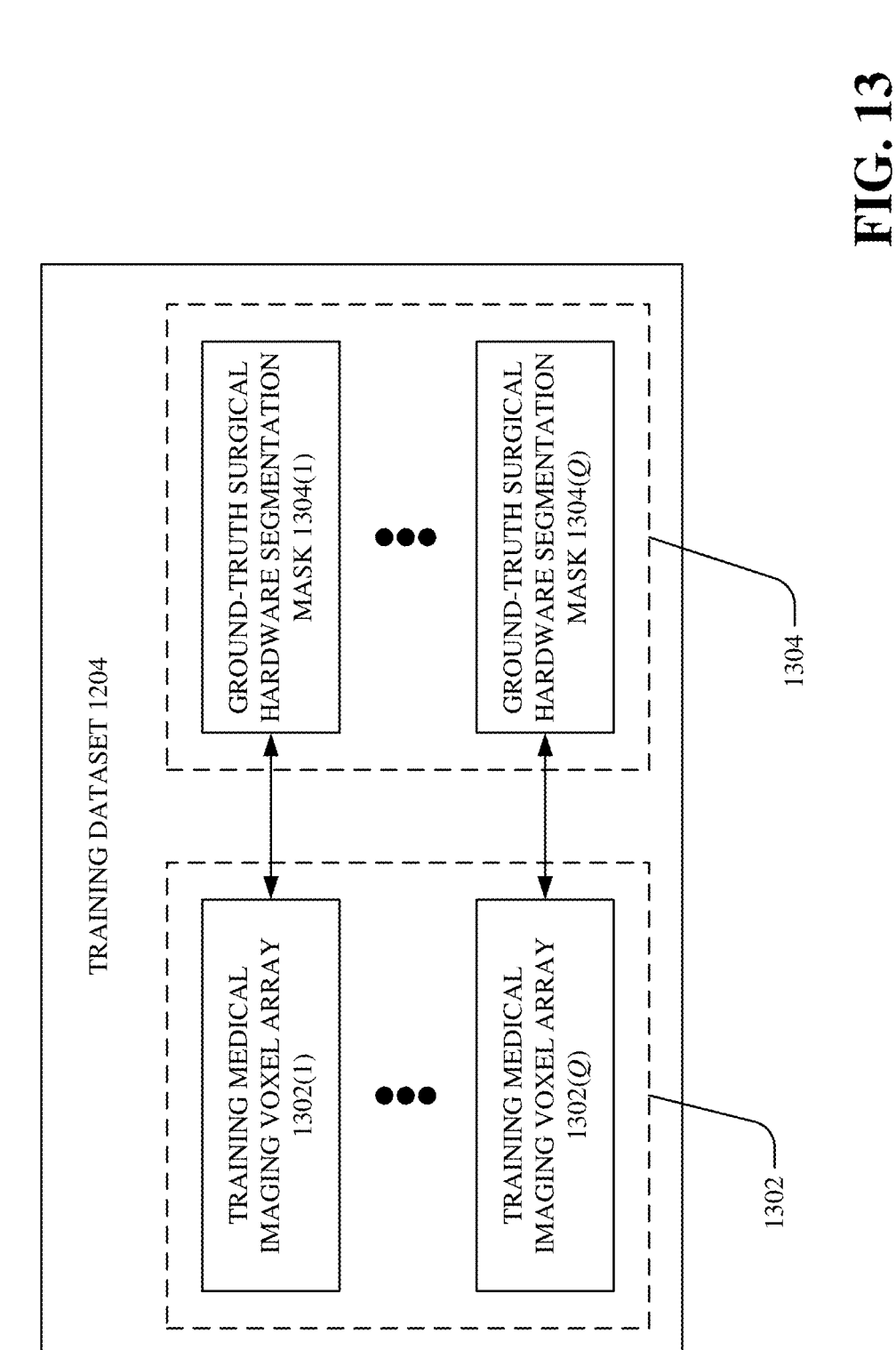
FIG. 13 illustrates an example, non-limiting block diagram of a training dataset in accordance with one or more embodiments described herein.

FIG. 13 illustrates an example, non-limiting block diagram 1300 of the training dataset 1204 in accordance with one or more embodiments described herein. As shown, the training dataset 1204 can, in various aspects, comprise a set of training medical imaging voxel arrays 1302. In various instances, the set of training medical imaging voxel arrays 1302 can comprise q voxel arrays for any suitable positive integer q: a training medical imaging voxel array 1302(1) to a training medical imaging voxel array 1302(q). In various cases, a training medical imaging voxel array can be any suitable electronic data having the same format, size, or dimensionality as the medical imaging voxel array 104. In other words, because the medical imaging voxel array 104 can be an x-by-y-by-z array of voxels, each of the set of training medical imaging voxel arrays 1302 can likewise be an x-by-y-by-z array of voxels. Moreover, in various cases, each of the set of training medical imaging voxel arrays 1302 can depict a respective spine of a respective medical patient, which respective spine may or may not have various surgically-inserted spinal hardware therein.

As also shown, the training dataset 1204 can comprise a set of ground-truth surgical hardware segmentation masks 1304. In various aspects, the set of ground-truth surgical hardware segmentation masks 1304 can respectively correspond to the set of training medical imaging voxel arrays 1302. Thus, since the set of training medical imaging voxel arrays 1302 can comprise q arrays, the set of ground-truth surgical hardware segmentation masks 1304 can comprise q masks: a ground-truth surgical hardware segmentation mask 1304(1) to a ground-truth surgical hardware segmentation mask 1304(q). In various instances, each of the set of ground-truth surgical hardware segmentation masks 1304 can have the same format, size, or dimensionality as the surgical hardware segmentation mask 204. In other words, each of the set of ground-truth surgical hardware segmentation masks 1304 can indicate which voxels (if any) of a respective training medical imaging voxel array are known or deemed to belong to surgically-inserted spinal hardware and which voxels of such respective training medical imaging voxel array are not. For example, the ground-truth surgical hardware segmentation mask 1304(1) can correspond to the training medical imaging voxel array 1302(1). Thus, the ground-truth surgical hardware segmentation mask 1304(1) can be considered as indicating which voxels of the training medical imaging voxel array 1302(1) are known or otherwise deemed to make up surgical hardware inserted in a spine depicted in the training medical imaging voxel array 1302(1). As another example, the ground-truth surgical hardware segmentation mask 1304(q) can correspond to the training medical imaging voxel array 1302(q). So, the ground-truth surgical hardware segmentation mask 1304(q) can be considered as indicating which voxels of the training medical imaging voxel array 1302(q) are known or otherwise deemed to make up surgical hardware inserted in a spine depicted in the training medical imaging voxel array 1302(q).

Recall that, as mentioned above, rather than being configured to generate segmentation masks, the deep learning neural network 202 can instead be configured to generate any other suitable type or format of localization data (e.g., bounding boxes, centroidal points). In such cases, the set of ground-truth surgical hardware segmentation masks 1304 can be replaced with a set of ground-truth surgical hardware localizations (e.g., ground-truth bounding boxes, ground-truth centroidal points).

Now, consider FIG. 14. As shown, FIG. 14 illustrates an example, non-limiting block diagram 1400 showing how the deep learning neural network 202 can be trained to generate surgical hardware segmentation masks in accordance with one or more embodiments described herein.

In various aspects, the training component 1202 can, prior to beginning training, initialize in any suitable fashion (e.g., random initialization) the trainable internal parameters of (e.g., convolutional kernels, weight matrices, bias values) of the deep learning neural network 202.

In various instances, the training component 1202 can select from the training dataset 1204 a training medical imaging voxel array 1402 and a ground-truth surgical hardware segmentation mask 1404 that corresponds to the training medical imaging voxel array 1402. In various cases, as shown, the training component 1202 can execute the deep learning neural network 202 on the training medical imaging voxel array 1402, thereby causing the deep learning neural network 202 to produce an output 1406. More specifically, the training component 1202 can feed the training medical imaging voxel array 1402 to an input layer of the deep learning neural network 202, the training medical imaging voxel array 1402 can complete a forward pass through one or more hidden layers of the deep learning neural network 202, and an output layer of the deep learning neural network 202 can compute the output 1406 based on activation maps generated by the one or more hidden layers of the deep learning neural network 202.

Note that, in various aspects, the dimensionality of the output 1406 can be controlled or otherwise determined by the number or neurons in the output layer of the deep learning neural network 202. That is, a desired dimensionality of the output 1406 can be achieved by adding neurons to or removing neurons from the output layer of the deep learning neural network 202.

In various aspects, the output 1406 can be considered as the predicted or inferred surgical hardware segmentation mask which the deep learning neural network 202 identifies as corresponding to the training medical imaging voxel array 1402. In contrast, the ground-truth surgical hardware segmentation mask 1404 can be considered as the correct or accurate segmentation mask that is known or deemed to correspond to the training medical imaging voxel array 1402. Note that, if the deep learning neural network 202 has so far undergone no or little training, then the output 1406 can be highly inaccurate. That is, the output 1406 can be very different (e.g., as measured by any suitable metric) from the ground-truth surgical hardware segmentation mask 1404.

In any case, the training component 1202 can compute one or more errors or losses (e.g., MAE, MSE, cross-entropy) between the output 1406 and the ground-truth surgical hardware segmentation mask 1404. In various instances, the training component 1202 can incrementally update, via backpropagation, the trainable internal parameters of the deep learning neural network 202, based on such computed errors or losses.

In various cases, the training component 1202 can repeat such execution and update procedure for each training medical imaging voxel array in the training dataset 1204. This can ultimately cause the trainable internal parameters of the deep learning neural network 202 to become iteratively optimized for accurately generating surgical hardware segmentation masks for inputted medical imaging voxel arrays. In various aspects, the training component 1202 can implement any suitable training batch sizes, any suitable training termination criteria, or any suitable error/loss functions for training the deep learning neural network 202.

Figure 15:
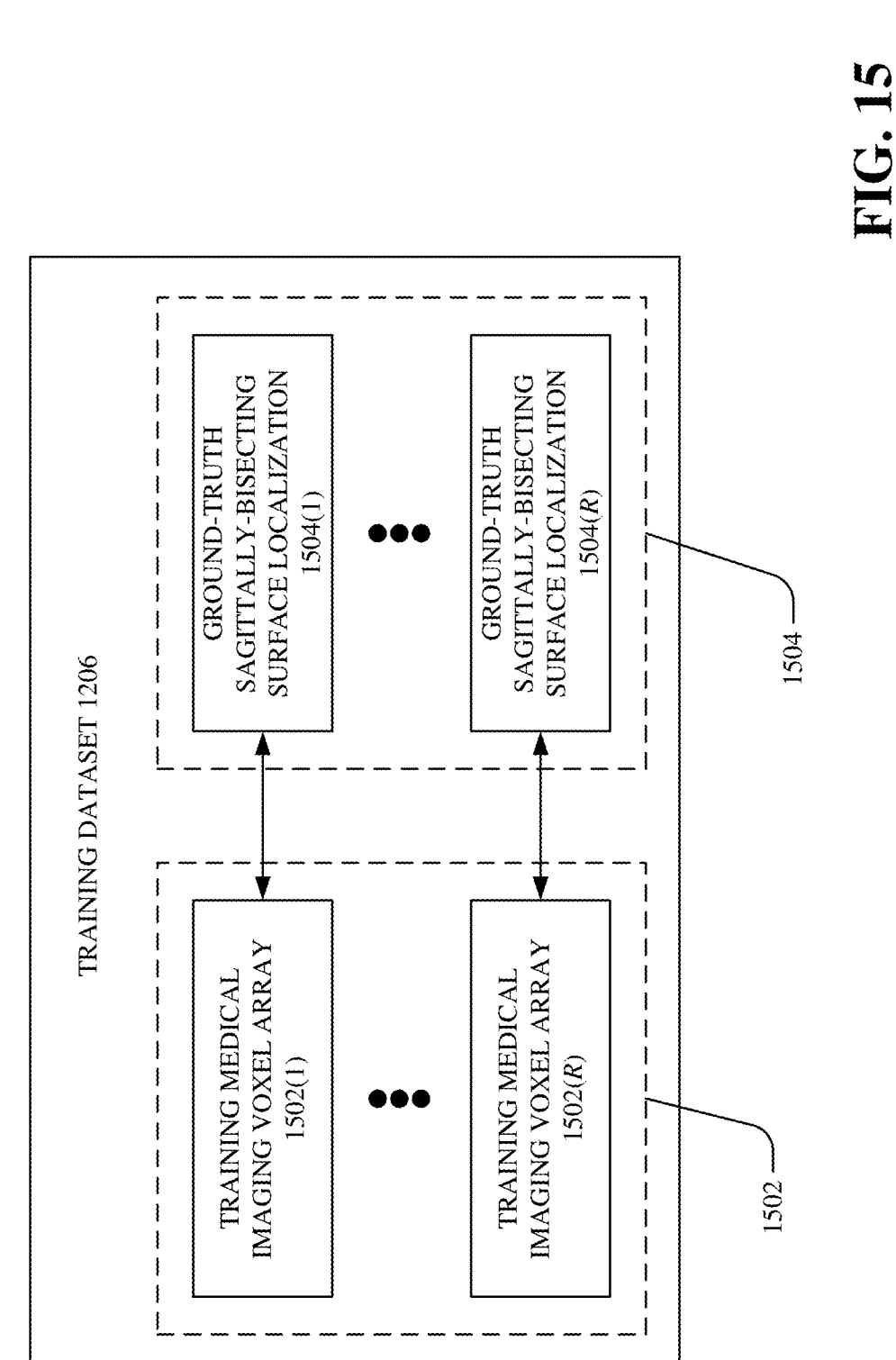
FIG. 15 illustrates an example, non-limiting block diagram of a training dataset in accordance with one or more embodiments described herein.

FIG. 15 illustrates an example, non-limiting block diagram 1500 of the training dataset 1206 in accordance with one or more embodiments described herein. As shown, the training dataset 1206 can, in various aspects, comprise a set of training medical imaging voxel arrays 1502. In various instances, the set of training medical imaging voxel arrays 1502 can comprise r voxel arrays for any suitable positive integer r: a training medical imaging voxel array 1502(1) to a training medical imaging voxel array 1502(r). In various cases, a training medical imaging voxel array can be as described above with respect to FIG. 13.

As also shown, the training dataset 1206 can comprise a set of ground-truth sagittally-bisecting surface localizations 1504. In various aspects, the set of ground-truth sagittally-bisecting surface localizations 1504 can respectively correspond to the set of training medical imaging voxel arrays 1502. Thus, since the set of training medical imaging voxel arrays 1502 can comprise r arrays, the set of ground-truth sagittally-bisecting surface localizations 1504 can comprise r localizations: a ground-truth sagittally-bisecting surface localization 1504(1) to a ground-truth sagittally-bisecting surface localization 1504(r). In various instances, each of the set of ground-truth sagittally-bisecting surface localizations 1504 can have the same format, size, or dimensionality as the sagittally-bisecting surface localization 404. In other words, each of the set of ground-truth sagittally-bisecting surface localizations 1504 can indicate or otherwise identify a planar or curved surface within a respective training medical imaging voxel array that is known or deemed to sagittally-bisect a spine depicted in such respective training medical imaging voxel array. For example, the ground-truth sagittally-bisecting surface localization 1504(1) can correspond to the training medical imaging voxel array 1502(1). Thus, the ground-truth sagittally-bisecting surface localization 1504(1) can be considered as indicating or identifying a planar or curved surface within the training medical imaging voxel array 1502(1) that is known or otherwise deemed to sagittally-bisect a spine depicted in the training medical imaging voxel array 1502(1). As another example, the ground-truth sagittally-bisecting surface localization 1504(r) can correspond to the training medical imaging voxel array 1502(r). So, the ground-truth sagittally-bisecting surface localization 1504(r) can be considered as indicating or identifying a planar or curved surface within the training medical imaging voxel array 1502(r) that is known or otherwise deemed to sagittally-bisect a spine depicted in the training medical imaging voxel array 1502(r).

Figure 16:
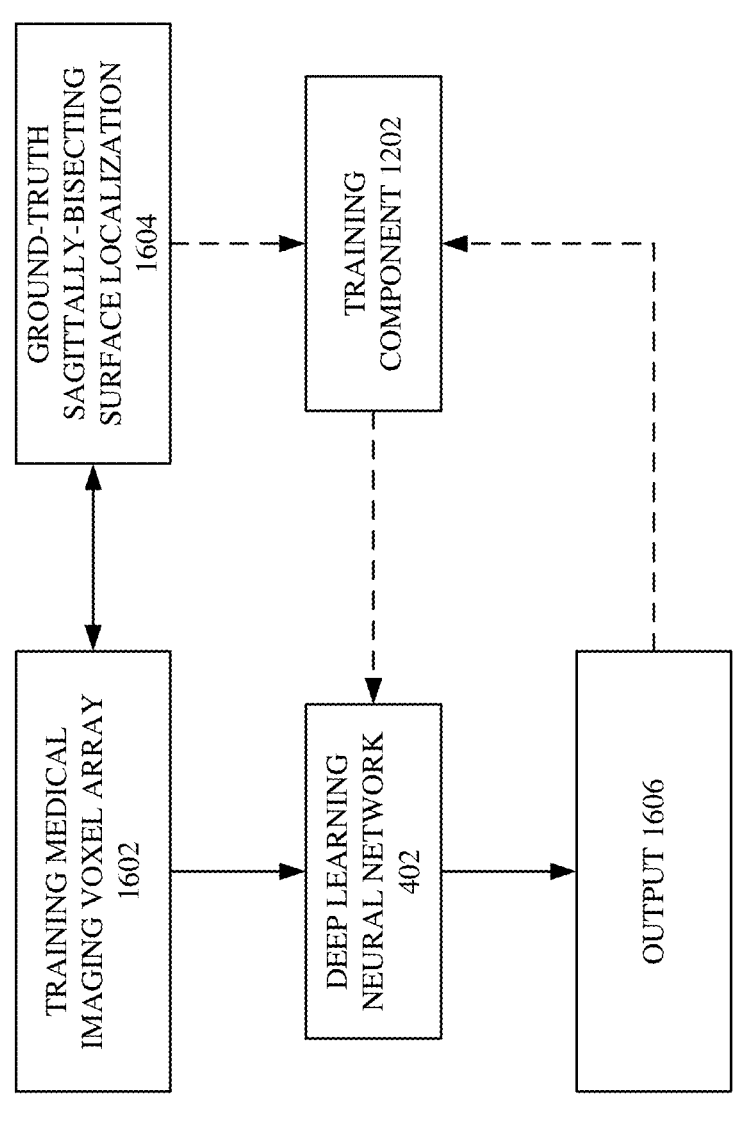
FIG. 16 illustrates an example, non-limiting block diagram showing how a deep learning neural network can be trained to localize sagittally-bisecting surfaces in accordance with one or more embodiments described herein.

Now, consider FIG. 16. As shown, FIG. 16 illustrates an example, non-limiting block diagram 1600 showing how the deep learning neural network 402 can be trained to generate sagittally-bisecting surface localizations in accordance with one or more embodiments described herein.

In various aspects, the training component 1202 can, prior to beginning training, initialize in any suitable fashion (e.g., random initialization) the trainable internal parameters of (e.g., convolutional kernels, weight matrices, bias values) of the deep learning neural network 402.

In various instances, the training component 1202 can select from the training dataset 1206 a training medical imaging voxel array 1602 and a ground-truth sagittally-bisecting surface localization 1604 that corresponds to the training medical imaging voxel array 1602. In various cases, as shown, the training component 1202 can execute the deep learning neural network 402 on the training medical imaging voxel array 1602, thereby causing the deep learning neural network 402 to produce an output 1606. More specifically, the training component 1202 can feed the training medical imaging voxel array 1602 to an input layer of the deep learning neural network 402, the training medical imaging voxel array 1602 can complete a forward pass through one or more hidden layers of the deep learning neural network 402, and an output layer of the deep learning neural network

402 can compute the output 1606 based on activation maps generated by the one or more hidden layers of the deep learning neural network 402.

Note that, as above, the dimensionality of the output 1606 can be controlled or otherwise determined by the number or neurons in the output layer of the deep learning neural network 402. In other words, a desired dimensionality of the output 1606 can be achieved by adding neurons to or removing neurons from the output layer of the deep learning neural network 402.

In various aspects, the output 1606 can be considered as the predicted or inferred sagittally-bisecting surface localization which the deep learning neural network 402 identifies as corresponding to the training medical imaging voxel array 1602. In contrast, the ground-truth sagittally-bisecting surface localization 1604 can be considered as the correct or accurate sagittally-bisecting surface localization that is known or deemed to correspond to the training medical imaging voxel array 1602. Note that, if the deep learning neural network 402 has so far undergone no or little training, then the output 1606 can be highly inaccurate. That is, the output 1606 can be very different (e.g., as measured via any suitable metric) from the ground-truth sagittally-bisecting surface localization 1604.

In any case, the training component 1202 can compute one or more errors or losses (e.g., MAE, MSE, cross-entropy) between the output 1606 and the ground-truth sagittally-bisecting surface localization 1604. In various instances, the training component 1202 can incrementally update, via backpropagation, the trainable internal parameters of the deep learning neural network 402, based on such computed errors or losses.

In various cases, the training component 1202 can repeat such execution and update procedure for each training medical imaging voxel array in the training dataset 1206. This can ultimately cause the trainable internal parameters of the deep learning neural network 402 to become iteratively optimized for accurately localizing sagittally-bisecting surfaces in inputted medical imaging voxel arrays. In various aspects, the training component 1202 can implement any suitable training batch sizes, any suitable training termination criteria, or any suitable error/loss functions for training the deep learning neural network 402.

FIG. 17 illustrates a flow diagram of an example, non-limiting computer-implemented method 1700 that can facilitate improved spinal hardware rendering in accordance with one or more embodiments described herein. In various cases, the spinal hardware rendition system 102 can perform the computer-implemented method 1700.

In various embodiments, act 1702 can include obtaining, by a device (e.g., via 114) operatively coupled to a processor, a medical imaging volume (e.g., 104) depicting a spine (e.g., 106) of a medical patient.

In various aspects, act 1704 can include determining, by the device (e.g., via 116) whether the medical imaging volume depicts surgical hardware (e.g., 108) inserted in the spine. If not, the computer-implemented method 1700 can proceed to act 1706. If so, the computer-implemented method 1700 can proceed instead to act 1708.

In various instances, act 1706 can include rendering, by the device (e.g., via 120) and on an electronic display, a notification indicating that no surgically-inserted spinal hardware has been detected in the medical imaging volume. In various cases, the computer-implemented method 1700 can proceed back to act 1702.

In various aspects, act 1708 can include localizing, by the device (e.g., via 118), a curved or planar surface (e.g., 702) within the medical imaging volume that sagittally-bisects the spine.

In various instances, act 1710 can include rendering, by the device (e.g., via 120) and on an electronic display, a butterfly-view (e.g., 802) of the medical imaging volume, where the butterfly-view can be hinged about the localized surface. In various cases, the butterfly-view can have a left window (e.g., 902) that depicts (e.g., via MIP or transparent VR) only image content of the medical imaging volume that is located leftward of the localized surface. Moreover, in various aspects, the butterfly-view can have a right window (e.g., 904) that depicts (e.g., via MIP or transparent VR) only image content of the medical imaging volume that is located rightward of the localized surface. Because surgically-inserted spinal hardware can often occur in sagittal counterparts or sagittal pairs, the butterfly-view can be considered as visually illustrating the various surgical hardware inserted in the spine, without superimposing the various surgical hardware on top of each other. In various cases, the computer-implemented method 1700 can proceed back to act 1702.

Figure 18:
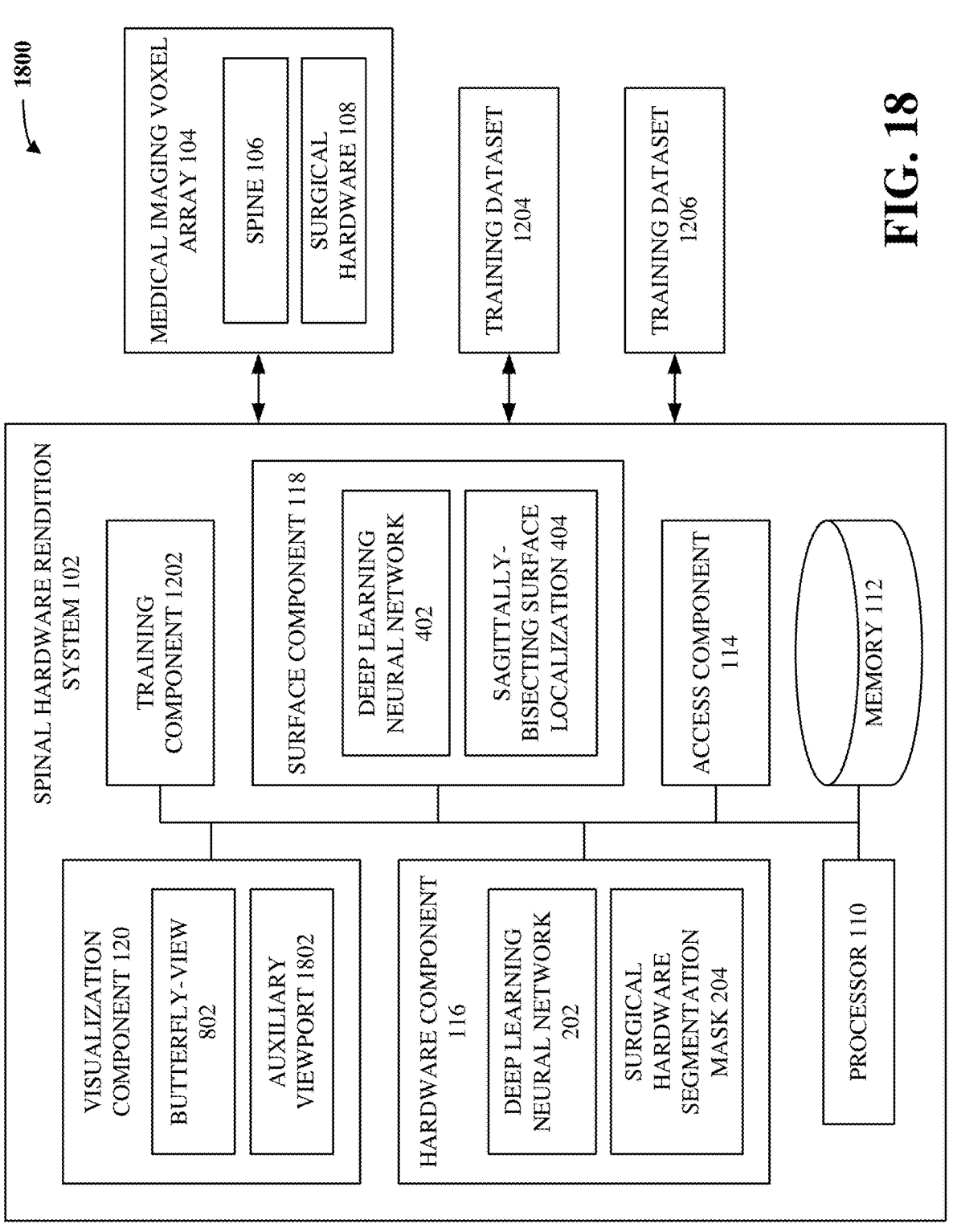
FIG. 18 illustrates a block diagram of an example, non-limiting system including an auxiliary viewport that facilitates improved spinal hardware rendering in accordance with one or more embodiments described herein.

FIG. 18 illustrates a block diagram of an example, non-limiting system 1800 including an auxiliary viewport that can facilitate improved spinal hardware rendering in accordance with one or more embodiments described herein. As shown, the system 1800 can, in some cases, comprise the same components as the system 1200, and can further comprise an auxiliary viewport 1802.

In various embodiments, the butterfly-view 802 can be interactive. In other words, a user, technician, or medical professional can interact with the butterfly-view 802 via any suitable human-computer interface device (not shown). Not limiting examples of such human-computer interface device can include keyboards, keypads, joysticks, touchscreens, or computer mice. In some cases, the user, technician, or medical professional can click, select, or otherwise invoke any of the set of surgical hardware 108 that are depicted in the butterfly-view 802, and the visualization component 120 can render, on any suitable electronic display, the auxiliary viewport 1802 in response to such clicking, selection, or invocation.

More specifically, as mentioned above, the surgical hardware segmentation mask 204 can, in some cases, multichotomously indicate which voxels of the medical imaging voxel array 104 (and thus which voxels projected in the butterfly-view 802) belong to which specific types of surgical hardware. For example, the surgical hardware segmentation mask 204 can, in some instances, indicate which voxels of the medical imaging voxel array 104 belong to spinal screws, which voxels of the medical imaging voxel array 104 belong to spinal rods, or which voxels of the medical imaging voxel array 104 belong to spinal plates. Accordingly, the visualization component 120 can identify distinct pieces of surgical hardware that are inserted in the spine 106, by analyzing the contiguity of different voxel-wise surgical hardware classes indicated by the surgical hardware segmentation mask 204.

As a non-limiting example, the surgical hardware segmentation mask 204 can indicate that h voxels within the medical imaging voxel array 104 belong to a surgical screw class, for any suitable positive integer h. However, such h voxels can form, due to their positions/locations within the medical imaging voxel array 104, i distinct, contiguous, non-adjacent islands of voxels, for any suitable positive integer i<h. Accordingly, by counting the number of distinct, contiguous, non-adjacent islands of voxels that belong to the spinal screw class, the visualization component 120 can identify i distinct spinal screws inserted into the spine 106.

As another non-limiting example, the surgical hardware segmentation mask 204 can indicate that j voxels within the medical imaging voxel array 104 belong to a surgical plate class, for any suitable positive integer j. However, such j voxels can form, due to their positions/locations within the medical imaging voxel array 104, k distinct, contiguous, non-adjacent islands of voxels, for any suitable positive integer k<j. Accordingly, by counting the number of distinct, contiguous, non-adjacent islands of voxels that belong to the spinal plate class, the visualization component 120 can identify k distinct spinal plates inserted into the spine 106.

In any case, the visualization component 120 can identify distinct pieces of surgically-inserted spinal hardware within the medical imaging voxel array 104 by analyzing the surgical hardware segmentation mask 204. In various aspects, when a user, technician, or medical professional clicks, selects, or otherwise invokes any one of such distinct pieces of surgically-inserted spinal hardware from the butterfly-view 802, the visualization component 120 can electronically render the auxiliary viewport 1802, where the auxiliary viewport 1802 can be a zoomed view of the clicked, selected, or invoked piece of surgically-inserted spinal hardware. In some cases, the auxiliary viewport 1802 can illustrate or depict any suitable projection, as rendered via an MIP technique or a transparent VR technique, of the clicked, selected, or invoked piece of surgically-inserted spinal hardware. As a non-limiting example, the auxiliary viewport 1802 can depict a longitudinal projection of the clicked, selected, or invoked piece of surgically-inserted spinal hardware. As another non-limiting example, the auxiliary viewport 1802 can depict an axial projection of the clicked, selected, or invoked piece of surgically-inserted spinal hardware. As even another non-limiting example, the auxiliary viewport 1802 can depict an oblique projection of the clicked, selected, or invoked piece of surgically-inserted spinal hardware.

In any case, the auxiliary viewport 1802 can help a medical professional to more quickly, easily, or thoroughly visually inspect the positions or orientations of the set of surgical hardware 108.

FIG. 19 illustrates a non-limiting example 1900 of the auxiliary viewport 1802 in accordance with one or more embodiments described herein.

As shown, there can be the butterfly-view 1004, as described above with respect to FIG. 10. In various cases, a medical professional that is visually inspecting the butterfly-view 1004 can click, via a computer mouse, on the bottom-most spinal screw depicted in the left side of the butterfly-view 1004. In response to that click, the visualization component 120 can generate an auxiliary viewport 1902, which can illustrate any suitable zoomed projection of such clicked spinal screw. In the non-limiting example shown in FIG. 19, the auxiliary viewport 1902 illustrates an oblique projection of the clicked spinal screw.

FIG. 20 illustrates a flow diagram of an example, non-limiting computer-implemented method 2000 that can facilitate improved spinal hardware rendering in accordance with one or more embodiments described herein. In various cases, the spinal hardware rendition system 102 can facilitate the computer-implemented method 2000.

In various embodiments, act 2002 can include accessing, by a device (e.g., via 114) operatively coupled to a processor, a medical imaging voxel array (e.g., 104) depicting a spine (e.g., 106) of a medical patient.

In various aspects, act 2004 can include determining, by the device (e.g., via 116), whether the medical imaging voxel array depicts a set of surgical hardware (e.g., 108) inserted in the spine of the medical patient.

In various instances, act 2006 can include localizing, by the device (e.g., via 118) and in response to a determination that the medical imaging voxel array depicts the set of surgical hardware, a surface (e.g., 702) that sagittally bisects the spine of the medical patient.

In various cases, act 2008 can include rendering, by the device (e.g., via 120) and on an electronic display, a butterfly-view (e.g., 802) of the medical imaging voxel array, wherein the butterfly-view can be hinged about the localized surface.

Although not explicitly shown in FIG. 20, the butterfly-view can comprise a left pane (e.g., 902) and a right pane (e.g., 904), wherein the left pane can depict voxels of the medical imaging voxel array that are leftward of the localized surface and that can depict no voxels of the medical imaging voxel array that are rightward of the localized surface, and wherein the right pane can depict voxels of the medical imaging voxel array that are rightward of the localized surface and that can depict no voxels of the medical imaging voxel array that are leftward of the localized surface.

Although not explicitly shown in FIG. 20, the butterfly-view can be rendered via a maximum intensity projection technique or a transparent volume-rendering technique.

Although not explicitly shown in FIG. 20, the localized surface can be a sagittal plane of the medical patient.

Although not explicitly shown in FIG. 20, the localized surface can be a curved surface.

Although not explicitly shown in FIG. 20, the computer-implemented method 2000 can further comprise: rendering, by the device (e.g., via 120), on the electronic display, and in response to at least one of the set of surgical hardware being clicked in the butterfly-view, an additional viewport (e.g., 1802) of the at least one of the set of surgical hardware. In various cases, the additional viewport can depict a zoomed axial view, a zoomed longitudinal view, or a zoomed oblique view of the at least one of the set of surgical hardware.

Although the herein disclosure mainly describes various embodiments as applying to deep learning neural networks (e.g., 202, 402), this is a mere non-limiting example. In various aspects, the herein-described teachings can be applied to any suitable machine learning models exhibiting any suitable artificial intelligence architectures (e.g., support vector machines, naïve Bayes, linear regression, logistic regression, decision trees, random forest). Moreover, in various instances, any suitable analytical techniques (e.g., non-artificial-intelligence techniques) can be implemented in place of the herein-described deep learning neural networks (e.g., in place of 202 or 402).

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by $f(z)=confidence(class)$. Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

The herein disclosure describes non-limiting examples. For ease of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

Figure 21:
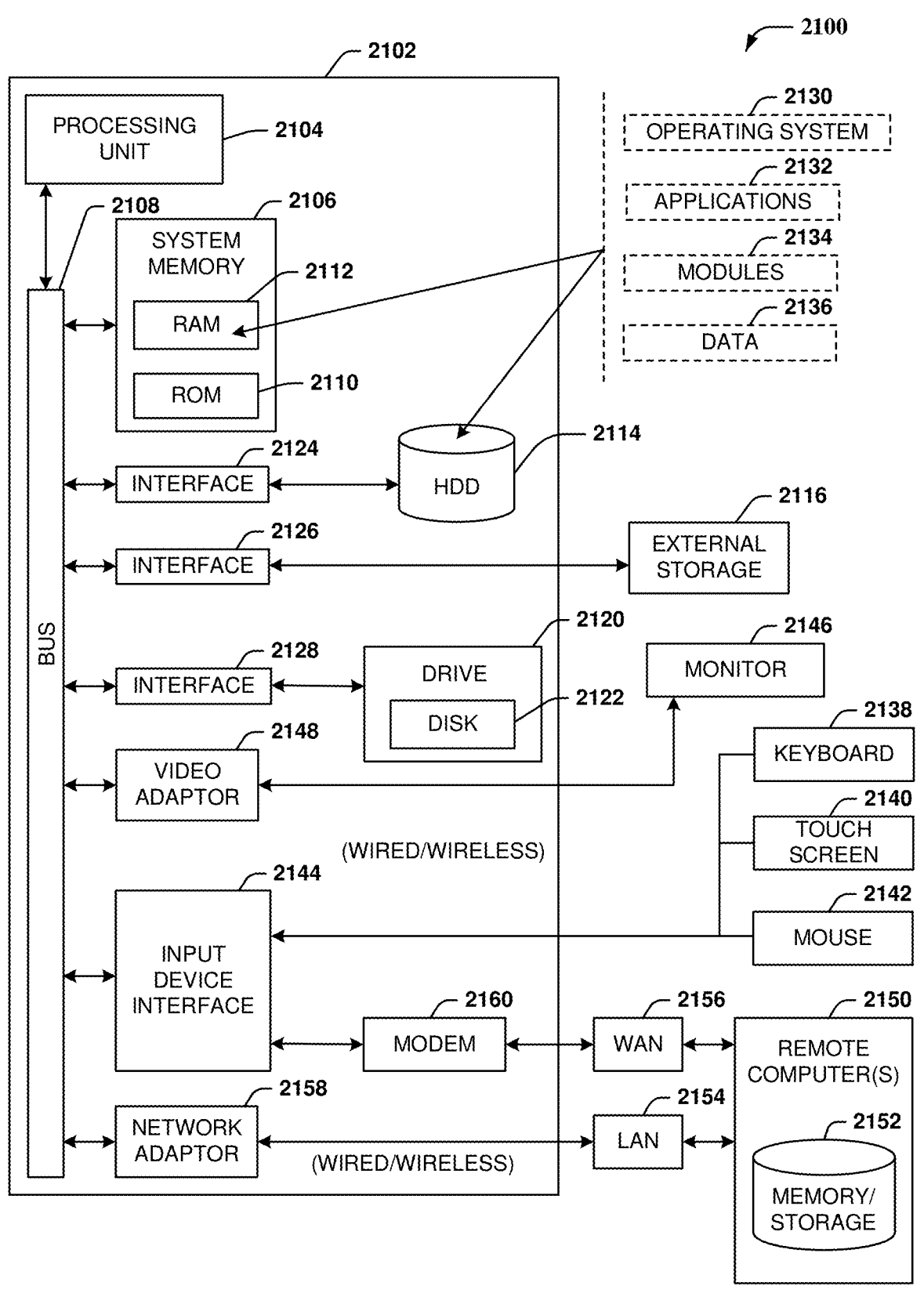
FIG. 21 illustrates a block diagram of an example, non-limiting operating environment in which one or more embodiments described herein can be facilitated.

In order to provide additional context for various embodiments described herein, FIG. 21 and the following discussion are intended to provide a brief, general description of a suitable computing environment 2100 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IOT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 21, the example environment 2100 for implementing various embodiments of the aspects described herein includes a computer 2102, the computer 2102 including a processing unit 2104, a system memory 2106 and a system bus 2108. The system bus 2108 couples system components including, but not limited to, the system memory 2106 to the processing unit 2104. The processing unit 2104 can be any of various commercially available processors. Dual microprocessors and other multi-processor architectures can also be employed as the processing unit 2104.

The system bus 2108 can be any of several types of bus structure that can further interconnect to a memory bus (with or without a memory controller), a peripheral bus, and a local bus using any of a variety of commercially available bus architectures. The system memory 2106 includes ROM 2110 and RAM 2112. A basic input/output system (BIOS) can be stored in a non-volatile memory such as ROM, erasable programmable read only memory (EPROM), EEPROM, which BIOS contains the basic routines that help to transfer information between elements within the computer 2102, such as during startup. The RAM 2112 can also include a high-speed RAM such as static RAM for caching data.

The computer 2102 further includes an internal hard disk drive (HDD) 2114 (e.g., EIDE, SATA), one or more external storage devices 2116 (e.g., a magnetic floppy disk drive (FDD) 2116, a memory stick or flash drive reader, a memory card reader, etc.) and a drive 2120, e.g., such as a solid state drive, an optical disk drive, which can read or write from a disk 2122, such as a CD-ROM disc, a DVD, a BD, etc. Alternatively, where a solid state drive is involved, disk 2122 would not be included, unless separate. While the internal HDD 2114 is illustrated as located within the computer 2102, the internal HDD 2114 can also be configured for external use in a suitable chassis (not shown). Additionally, while not shown in environment 2100, a solid state drive (SSD) could be used in addition to, or in place of, an HDD 2114. The HDD 2114, external storage device(s) 2116 and drive 2120 can be connected to the system bus 2108 by an HDD interface 2124, an external storage interface 2126 and a drive interface 2128, respectively. The interface 2124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2112, including an operating system 2130, one or more application programs 2132, other program modules 2134 and program data 2136. All or portions of the operating system, applications, modules, or data can also be cached in the RAM 2112. The systems and methods described herein can be implemented utilizing various commercially available operating systems or combinations of operating systems.

Computer 2102 can optionally comprise emulation technologies. For example, a hypervisor (not shown) or other intermediary can emulate a hardware environment for operating system 2130, and the emulated hardware can optionally be different from the hardware illustrated in FIG. 21. In such an embodiment, operating system 2130 can comprise one virtual machine (VM) of multiple VMs hosted at computer 2102. Furthermore, operating system 2130 can provide runtime environments, such as the Java runtime environment or the .NET framework, for applications 2132. Runtime environments are consistent execution environments that allow applications 2132 to run on any operating system that includes the runtime environment. Similarly, operating system 2130 can support containers, and applications 2132 can be in the form of containers, which are lightweight, standalone, executable packages of software that include, e.g., code, runtime, system tools, system libraries and settings for an application.

Further, computer 2102 can be enable with a security module, such as a trusted processing module (TPM). For instance with a TPM, boot components hash next in time boot components, and wait for a match of results to secured values, before loading a next boot component. This process can take place at any layer in the code execution stack of computer 2102, e.g., applied at the application execution level or at the operating system (OS) kernel level, thereby enabling security at any level of code execution.

A user can enter commands and information into the computer 2102 through one or more wired/wireless input devices, e.g., a keyboard 2138, a touch screen 2140, and a pointing device, such as a mouse 2142. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2104 through an input device interface 2144 that can be coupled to the system bus 2108, but can be connected by other interfaces, such as a parallel port, an IEEE 1394 serial port, a game port, a USB port, an IR interface, a BLUETOOTH® interface, etc.

A monitor 2146 or other type of display device can be also connected to the system bus 2108 via an interface, such as a video adapter 2148. In addition to the monitor 2146, a computer typically includes other peripheral output devices (not shown), such as speakers, printers, etc.

The computer 2102 can operate in a networked environment using logical connections via wired or wireless communications to one or more remote computers, such as a remote computer(s) 2150. The remote computer(s) 2150 can be a workstation, a server computer, a router, a personal computer, portable computer, microprocessor-based entertainment appliance, a peer device or other common network node, and typically includes many or all of the elements described relative to the computer 2102, although, for purposes of brevity, only a memory/storage device 2152 is illustrated. The logical connections depicted include wired/wireless connectivity to a local area network (LAN) 2154 or larger networks, e.g., a wide area network (WAN) 2156. Such LAN and WAN networking environments are commonplace in offices and companies, and facilitate enterprise-wide computer networks, such as intranets, all of which can connect to a global communications network, e.g., the Internet.

When used in a LAN networking environment, the computer 2102 can be connected to the local network 2154 through a wired or wireless communication network interface or adapter 2158. The adapter 2158 can facilitate wired or wireless communication to the LAN 2154, which can also include a wireless access point (AP) disposed thereon for communicating with the adapter 2158 in a wireless mode.

When used in a WAN networking environment, the computer 2102 can include a modem 2160 or can be connected to a communications server on the WAN 2156 via other means for establishing communications over the WAN 2156, such as by way of the Internet. The modem 2160, which can be internal or external and a wired or wireless device, can be connected to the system bus 2108 via the input device interface 2144. In a networked environment, program modules depicted relative to the computer 2102 or portions thereof, can be stored in the remote memory/storage device 2152. It will be appreciated that the network connections shown are example and other means of establishing a communications link between the computers can be used.

When used in either a LAN or WAN networking environment, the computer 2102 can access cloud storage systems or other network-based storage systems in addition to, or in place of, external storage devices 2116 as described above, such as but not limited to a network virtual machine providing one or more aspects of storage or processing of information. Generally, a connection between the computer 2102 and a cloud storage system can be established over a LAN 2154 or WAN 2156 e.g., by the adapter 2158 or modem 2160, respectively. Upon connecting the computer 2102 to an associated cloud storage system, the external storage interface 2126 can, with the aid of the adapter 2158 or modem 2160, manage storage provided by the cloud storage system as it would other types of external storage. For instance, the external storage interface 2126 can be configured to provide access to cloud storage sources as if those sources were physically connected to the computer 2102.

The computer 2102 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

FIG. 22 is a schematic block diagram of a sample computing environment 2200 with which the disclosed subject matter can interact. The sample computing environment 2200 includes one or more client(s) 2210. The client(s) 2210 can be hardware or software (e.g., threads, processes, computing devices). The sample computing environment 2200 also includes one or more server(s) 2230. The server(s) 2230 can also be hardware or software (e.g., threads, processes, computing devices). The servers 2230 can house threads to perform transformations by employing one or more embodiments as described herein, for example. One possible communication between a client 2210 and a server 2230 can be in the form of a data packet adapted to be transmitted between two or more computer processes. The sample computing environment 2200 includes a communication framework 2250 that can be employed to facilitate communications between the client(s) 2210 and the server(s) 2230. The client(s) 2210 are operably connected to one or more client data store(s) 2220 that can be employed to store information local to the client(s) 2210. Similarly, the server(s) 2230 are operably connected to one or more server data store(s) 2240 that can be employed to store information local to the servers 2230.

The present invention may be a system, a method, an apparatus or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations or block diagrams of methods, apparatus (systems), and computer program products according to embodiments of the invention. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising: a processor that executes computer-executable components stored in a non-transitory computer-readable memory, the computer-executable components comprising: an access component that accesses a medical imaging voxel array depicting a spine of a medical patient; a hardware component that determines whether the medical imaging voxel array depicts a set of surgical hardware inserted in the spine of the medical patient; a surface component that, in response to a determination that the medical imaging voxel array depicts the set of surgical hardware, localizes a surface that sagittally bisects the spine of the medical patient; and a visualization component that renders, on an electronic display, a butterfly-view of the medical imaging voxel array, wherein the butterfly-view is hinged about the localized surface, wherein the butterfly-view comprises a left pane and a right pane, wherein the left pane depicts voxels of the medical imaging voxel array that are leftward of the localized surface and that depicts no voxels of the medical imaging voxel array that are rightward of the localized surface, and wherein the right pane depicts voxels of the medical imaging voxel array that are rightward of the localized surface and that depicts no voxels of the medical imaging voxel array that are leftward of the localized surface.

2. The system of claim 1, wherein the visualization component renders the butterfly-view via a maximum intensity projection technique or a transparent volume-rendering technique.

3. The system of claim 1, wherein the localized surface is a sagittal plane of the medical patient.

4. The system of claim 1, wherein the localized surface is a curved surface.

5. The system of claim 1, wherein, in response to at least one of the set of surgical hardware being clicked in the butterfly-view, the visualization component renders, on the electronic display, an additional viewport of the at least one of the set of surgical hardware.

6. The system of claim 5, wherein the additional viewport depicts a zoomed axial view, a zoomed longitudinal view, or a zoomed oblique view of the at least one of the set of surgical hardware.

7. A computer-implemented method, comprising: accessing, by a device operatively coupled to a processor, a medical imaging voxel array depicting a spine of a medical patient; determining, by the device, whether the medical imaging voxel array depicts a set of surgical hardware inserted in the spine of the medical patient; localizing, by the device and in response to a determination that the medical imaging voxel array depicts the set of surgical hardware, a surface that sagittally bisects the spine of the medical patient; and rendering, by the device and on an electronic display, a butterfly-view of the medical imaging voxel array, wherein the butterfly-view is hinged about the localized surface, wherein the butterfly-view comprises a left pane and a right pane, wherein the left pane depicts voxels of the medical imaging voxel array that are leftward of the localized surface and that depicts no voxels of the medical imaging voxel array that are rightward of the localized surface, and wherein the right pane depicts voxels of the medical imaging voxel array that are rightward of the localized surface and that depicts no voxels of the medical imaging voxel array that are leftward of the localized surface.

8. The computer-implemented method of claim 7, wherein the butterfly-view is rendered via a maximum intensity projection technique or a transparent volume-rendering technique.

9. The computer-implemented method of claim 7, wherein the localized surface is a sagittal plane of the medical patient.

10. The computer-implemented method of claim 7, wherein the localized surface is a curved surface.

11. The computer-implemented method of claim 7, further comprising:

rendering, by the device, on the electronic display, and in response to at least one of the set of surgical hardware being clicked in the butterfly-view, an additional viewport of the at least one of the set of surgical hardware.

12. The computer-implemented method of claim 11, wherein the additional viewport depicts a zoomed axial view, a zoomed longitudinal view, or a zoomed oblique view of the at least one of the set of surgical hardware.

13. A computer program product for facilitating improved spinal hardware rendering, the computer program product comprising a non-transitory computer-readable memory having program instructions embodied therewith, the program instructions executable by a processor to cause the processor to: access a medical imaging voxel array depicting a spine of a medical patient; determine whether the medical imaging voxel array depicts a set of surgical hardware inserted in the spine of the medical patient; localize, in response to a determination that the medical imaging voxel array depicts the set of surgical hardware, a surface that sagittally bisects the spine of the medical patient; and render, on an electronic display, a butterfly-view of the medical imaging voxel array, wherein the butterfly-view is hinged about the localized surface, wherein the butterfly-view comprises a left pane and a right pane, wherein the left pane depicts voxels of the medical imaging voxel array that are leftward of the localized surface and that depicts no voxels of the medical imaging voxel array that are rightward of the localized surface, and wherein the right pane depicts voxels of the medical imaging voxel array that are rightward of the localized surface and that depicts no voxels of the medical imaging voxel array that are leftward of the localized surface.

14. The computer program product of claim 13, wherein the processor renders the butterfly-view via a maximum intensity projection technique or a transparent volume-rendering technique.

15. The computer program product of claim 13, wherein the localized surface is a sagittal plane of the medical patient.

16. The computer program product of claim 13, wherein the localized surface is a curved surface.

17. The computer program product of claim 13, wherein the processor localizes the surgical hardware via a segmentation mask, one or more bounding boxes, or one or more centroidal points.

* * * * *